(12) United States Patent
Miller et al.

(10) Patent No.: US 8,202,229 B2
(45) Date of Patent: Jun. 19, 2012

(54) SURGICAL DEVICE

(75) Inventors: Michael E. Miller, Trafalgar, IN (US);
Jake Flagle, Indianapolis, IN (US);
Joseph L. Mark, Indianapolis, IN (US);
Zachary R. Nicoson, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 402 days.

(21) Appl. No.: 11/865,092

(22) Filed: Oct. 1, 2007

(65) Prior Publication Data
US 2009/0088666 A1 Apr. 2, 2009

(51) Int. Cl.
*A61B 10/02* (2006.01)
(52) U.S. Cl. .................................................. 600/568
(58) Field of Classification Search .......... 600/562, 600/564, 565, 566, 567, 568
See application file for complete search history.

(56) References Cited

U.S. PATENT DOCUMENTS

| | | |
|---|---|---|
| 1,337,733 A | 4/1920 | Sweetland et al. |
| 1,693,741 A | 12/1928 | Wuest |
| 1,734,652 A | 11/1929 | Sweetland |
| 1,941,982 A | 1/1934 | Gill |
| 2,047,714 A | 7/1936 | Smith |
| 2,656,930 A | 10/1953 | De Vries |
| 2,689,048 A | 9/1954 | Powers |
| 3,456,806 A | 1/1967 | Borston |
| 3,401,684 A | 9/1968 | Dremann |
| 3,561,429 A | 2/1971 | Jewett et al. |
| 3,732,858 A | 5/1973 | Banko |
| 3,734,099 A | 5/1973 | Bender et al. |
| 3,785,380 A | 1/1974 | Brumfield |
| 3,815,604 A | 6/1974 | O'Malley et al. |
| 3,833,000 A | 9/1974 | Bridgman |
| 3,844,272 A | 10/1974 | Banko |
| 3,889,657 A | 6/1975 | Baumgarten |
| 3,890,712 A | 6/1975 | Lopez |
| 3,937,222 A | 2/1976 | Banko |
| 3,938,505 A | 2/1976 | Jamshidi |
| 3,945,375 A | 3/1976 | Banko |
| 3,994,297 A | 11/1976 | Kopf |

(Continued)

FOREIGN PATENT DOCUMENTS
DE 9112550 11/1991
(Continued)

OTHER PUBLICATIONS

Final Office Action dated Feb. 27, 2009 for U.S. Appl. No. 12/031,423.

(Continued)

*Primary Examiner* — Max Hindenburg
*Assistant Examiner* — Michael C Stout
(74) *Attorney, Agent, or Firm* — Vista IP Law Group LLP

(57) ABSTRACT

A surgical device is disclosed. The surgical device comprises an outer sleeve, a cutting element, a spool, a piston, and a spring. The cutting element extends from the outer sleeve at the distal end of the outer sleeve. The cutting element comprises an outer cannula and an inner cannula. The spool is engaged with the outer cannula. The piston is engaged with the inner cannula. A spring is positioned between the spool and the piston. The spool is translated distally to translate the outer cannula towards the distal end. And the piston translates the inner cannula towards the distal end to sever tissue.

18 Claims, 30 Drawing Sheets

U.S. PATENT DOCUMENTS

| | | |
|---|---|---|
| 3,996,935 A | 12/1976 | Banko |
| 4,007,742 A | 2/1977 | Banko |
| 243,559 A | 3/1977 | Hoyle et al. |
| 4,019,514 A | 4/1977 | Banko |
| 4,083,706 A | 4/1978 | Wiley |
| 4,101,756 A | 7/1978 | Yamano |
| 4,117,843 A | 10/1978 | Banko |
| 4,159,773 A | 7/1979 | Losenno |
| 4,167,943 A | 9/1979 | Banko |
| 4,167,944 A | 9/1979 | Banko |
| 4,177,814 A | 12/1979 | Knepshield et al. |
| 4,203,444 A | 5/1980 | Bonnell et al. |
| 4,210,146 A | 7/1980 | Banko |
| 4,221,225 A | 9/1980 | Sloan et al. |
| 4,257,425 A | 3/1981 | Ryan |
| 4,282,098 A | 8/1981 | Morgan, Jr. |
| 4,308,878 A | 1/1982 | Silva |
| 4,316,465 A | 2/1982 | Dotson, Jr. |
| 4,320,761 A | 3/1982 | Haddad |
| 4,354,093 A | 10/1982 | Zago |
| 4,368,734 A | 1/1983 | Banko |
| 4,382,808 A | 5/1983 | Van Wormer, Jr. et al. |
| 4,393,879 A | 7/1983 | Milgrom |
| 4,468,217 A | 8/1984 | Kuzmick et al. |
| 4,513,745 A | 4/1985 | Amoils |
| 4,517,977 A | 5/1985 | Frost et al. |
| 4,530,356 A | 7/1985 | Helfgott et al. |
| 4,533,818 A | 8/1985 | Green |
| 4,549,554 A | 10/1985 | Markham |
| 4,562,838 A | 1/1986 | Walker |
| 4,644,951 A | 2/1987 | Bays |
| 4,651,753 A | 3/1987 | Lifton |
| 4,696,298 A | 9/1987 | Higgins et al. |
| 4,708,147 A | 11/1987 | Haaga |
| 4,781,198 A | 11/1988 | Kanabrocki |
| 4,803,341 A | 2/1989 | Barowski et al. |
| 4,817,631 A | 4/1989 | Schnepp-Pesch et al. |
| 4,850,373 A | 7/1989 | Zatloukal et al. |
| 4,871,074 A | 10/1989 | Bryson et al. |
| 4,886,492 A | 12/1989 | Brooke et al. |
| 4,893,635 A | 1/1990 | de Groot et al. |
| 4,919,146 A | 4/1990 | Rhinehart et al. |
| 4,926,877 A | 5/1990 | Bookwalter |
| RE33,258 E | 7/1990 | Onik et al. |
| 4,973,019 A | 11/1990 | Baird et al. |
| 4,982,739 A | 1/1991 | Hemstreet et al. |
| 4,985,027 A | 1/1991 | Dressel |
| 4,989,614 A | 2/1991 | Dejter, Jr. et al. |
| 4,995,877 A | 2/1991 | Ams et al. |
| 5,027,827 A | 7/1991 | Cody et al. |
| 5,031,778 A | 7/1991 | Edgecombe |
| 5,054,615 A | 10/1991 | Stillwagon et al. |
| 5,074,311 A | 12/1991 | Hasson |
| 5,090,649 A | 2/1992 | Tipp |
| 5,108,381 A | 4/1992 | Kolozsi |
| 5,112,299 A | 5/1992 | Pascaloff |
| 5,124,532 A | 6/1992 | Hafey et al. |
| 5,133,359 A | 7/1992 | Kedem et al. |
| 5,141,189 A | 8/1992 | Andrew |
| 329,304 A | 9/1992 | Tipp |
| 5,172,701 A | 12/1992 | Leigh |
| 332,670 A | 1/1993 | McFarland |
| 5,183,052 A | 2/1993 | Terwilliger |
| 5,192,439 A | 3/1993 | Roth et al. |
| 5,197,484 A | 3/1993 | Kornberg et al. |
| 5,197,968 A | 3/1993 | Clement |
| 5,213,110 A | 5/1993 | Kedem et al. |
| 5,217,478 A | 6/1993 | Rexroth |
| 5,217,479 A | 6/1993 | Shuler |
| 5,226,909 A | 7/1993 | Evans et al. |
| 5,234,000 A | 8/1993 | Hakky et al. |
| 5,243,994 A | 9/1993 | Ranalletta |
| 5,256,160 A | 10/1993 | Clement |
| 342,585 A | 12/1993 | Fischbach et al. |
| 5,275,609 A | 1/1994 | Pingleton et al. |
| 5,281,197 A | 1/1994 | Arias et al. |
| 5,284,156 A | 2/1994 | Schramm et al. |
| 5,285,795 A | 2/1994 | Ryan et al. |
| 5,289,831 A | 3/1994 | Bosley |
| 5,290,303 A | 3/1994 | Pingleton et al. |
| 5,295,980 A | 3/1994 | Ersek |
| 5,312,425 A | 5/1994 | Evans et al. |
| 5,320,110 A | 6/1994 | Wang |
| 5,320,635 A | 6/1994 | Smith |
| 5,348,022 A | 9/1994 | Leigh et al. |
| 5,353,804 A | 10/1994 | Kornberg et al. |
| 5,358,638 A | 10/1994 | Gershenson |
| 5,403,276 A | 4/1995 | Schechter et al. |
| 5,411,513 A | 5/1995 | Ireland et al. |
| 5,415,169 A | 5/1995 | Siczek et al. |
| 5,423,844 A | 6/1995 | Miller |
| 5,429,138 A | 7/1995 | Jamshidi |
| 5,431,645 A | 7/1995 | Smith et al. |
| 5,455,766 A | 10/1995 | Scheller et al. |
| 5,456,267 A | 10/1995 | Stark |
| 5,458,112 A | 10/1995 | Weaver |
| 5,464,300 A | 11/1995 | Crainich |
| 5,505,210 A | 4/1996 | Clement |
| 5,520,635 A | 5/1996 | Gelbfish |
| 5,520,801 A | 5/1996 | Gerber et al. |
| 371,220 A | 6/1996 | Behrens |
| 5,526,822 A | 6/1996 | Burbank et al. |
| 5,533,708 A | 7/1996 | Atkinson et al. |
| 5,543,695 A | 8/1996 | Culp et al. |
| 5,560,373 A | 10/1996 | De Santis |
| 5,575,293 A | 11/1996 | Miller et al. |
| 5,580,347 A | 12/1996 | Reimels |
| 377,996 A | 2/1997 | Gilbert |
| 5,601,585 A | 2/1997 | Banik et al. |
| 5,615,782 A | 4/1997 | Choe |
| 379,554 A | 5/1997 | Landers |
| 5,630,939 A | 5/1997 | Bulard et al. |
| 5,643,304 A | 7/1997 | Schechter et al. |
| 5,647,374 A | 7/1997 | Cutrer |
| 5,649,547 A | 7/1997 | Ritchart et al. |
| 5,669,876 A | 9/1997 | Schechter et al. |
| 5,669,923 A | 9/1997 | Gordon |
| 386,818 A | 11/1997 | Boomfield |
| 5,685,840 A | 11/1997 | Schechter et al. |
| 5,685,852 A | 11/1997 | Turkel et al. |
| 5,689,159 A | 11/1997 | Culp et al. |
| 5,730,717 A | 3/1998 | Gelbfish |
| 5,741,272 A * | 4/1998 | Kuhne ........................ 606/128 |
| 5,769,086 A | 6/1998 | Ritchart et al. |
| 5,775,333 A | 7/1998 | Burbank et al. |
| 5,779,649 A | 7/1998 | Herbert |
| 5,782,764 A | 7/1998 | Werne |
| 5,782,849 A | 7/1998 | Miller |
| 5,788,651 A | 8/1998 | Weilandt |
| 5,791,908 A | 8/1998 | Gillio |
| 5,794,626 A * | 8/1998 | Kieturakis .................... 600/567 |
| 5,794,799 A | 8/1998 | Collins et al. |
| 5,804,936 A | 9/1998 | Brodsky et al. |
| 5,810,806 A | 9/1998 | Ritchart et al. |
| 5,817,048 A | 10/1998 | Lawandy |
| 5,843,111 A | 12/1998 | Vijfvinkel |
| 5,848,978 A | 12/1998 | Cecchi |
| 403,810 A | 1/1999 | Owens |
| 5,871,454 A | 2/1999 | Majlessi |
| 5,893,862 A | 4/1999 | Pratt et al. |
| 5,910,139 A | 6/1999 | Cochran et al. |
| 5,911,701 A | 6/1999 | Miller et al. |
| 5,913,857 A | 6/1999 | Ritchart et al. |
| 5,916,229 A | 6/1999 | Evans |
| 5,928,164 A | 7/1999 | Burbank et al. |
| 5,928,218 A | 7/1999 | Gelbfish |
| 5,938,604 A | 8/1999 | Wagner et al. |
| 5,944,673 A | 8/1999 | Gregoire et al. |
| 5,964,716 A | 10/1999 | Gregoire et al. |
| 5,976,164 A | 11/1999 | Bencini et al. |
| 5,980,469 A * | 11/1999 | Burbank et al. ............... 600/567 |
| 5,980,546 A | 11/1999 | Hood |
| 5,997,560 A | 12/1999 | Miller |
| 6,007,497 A | 12/1999 | Huitema |
| 6,017,316 A | 1/2000 | Ritchart et al. |
| 6,019,733 A | 2/2000 | Farascioni |
| 6,022,324 A | 2/2000 | Skinner |

| | | | |
|---|---|---|---|
| 423,717 | A | 4/2000 | Taylor |
| 6,050,955 | A | 4/2000 | Bryan et al. |
| 426,025 | A | 5/2000 | Holmes et al. |
| 6,077,230 | A | 6/2000 | Gregoire et al. |
| 6,077,231 | A | 6/2000 | Milliman et al. |
| 6,080,113 | A | 6/2000 | Heneveld et al. |
| 6,085,749 | A | 7/2000 | Wardle et al. |
| 6,086,544 | A | 7/2000 | Hibner et al. |
| 6,096,042 | A | 8/2000 | Herbert |
| 6,106,512 | A | 8/2000 | Cochran et al. |
| 6,109,446 | A | 8/2000 | Foote |
| 6,120,462 | A | 9/2000 | Hibner et al. |
| 6,120,463 | A | 9/2000 | Bauer |
| 6,123,299 | A | 9/2000 | Zach, Sr. |
| 6,142,955 | A | 11/2000 | Farascioni et al. |
| 6,161,034 | A | 12/2000 | Burbank et al. |
| 6,162,187 | A | 12/2000 | Buzzard et al. |
| 6,193,414 | B1 | 2/2001 | Balzano |
| 6,193,673 | B1 | 2/2001 | Voila et al. |
| 6,213,988 | B1 | 4/2001 | McIvor et al. |
| 6,245,084 | B1 | 6/2001 | Mark et al. |
| 6,251,418 | B1 | 6/2001 | Ahern et al. |
| 6,273,862 | B1 | 8/2001 | Privitera et al. |
| 6,276,661 | B1 | 8/2001 | Laird |
| 6,280,399 | B1 | 8/2001 | Rossin et al. |
| 6,293,957 | B1 | 9/2001 | Peters et al. |
| 6,331,165 | B1 | 12/2001 | Turturro et al. |
| 6,332,891 | B1 | 12/2001 | Himes |
| 6,346,107 | B1 | 2/2002 | Cucin |
| 6,347,241 | B2 | 2/2002 | Burbank et al. |
| 6,402,701 | B1 | 6/2002 | Kaplan et al. |
| 6,428,487 | B1 | 8/2002 | Burdorff et al. |
| 6,436,054 | B1 | 8/2002 | Viola et al. |
| 6,461,350 | B1 | 10/2002 | Underwood et al. |
| 6,468,225 | B1 | 10/2002 | Lundgren |
| 6,468,227 | B2 | 10/2002 | Zimmon |
| 6,471,700 | B1 | 10/2002 | Burbank et al. |
| 6,485,436 | B1 | 11/2002 | Truckai et al. |
| 6,494,844 | B1 | 12/2002 | Van Bladel et al. |
| 6,592,508 | B1 | 7/2003 | Ravins et al. |
| 6,602,227 | B1 | 8/2003 | Cimino et al. |
| 6,626,849 | B2 | 9/2003 | Huitema et al. |
| 6,632,182 | B1 | 10/2003 | Treat |
| 6,638,235 | B2 | 10/2003 | Miller et al. |
| 6,676,658 | B2 | 1/2004 | Burbank et al. |
| 6,712,773 | B1 | 3/2004 | Viola |
| 6,725,083 | B1 | 4/2004 | Burbank et al. |
| 6,730,044 | B2 | 5/2004 | Stephens et al. |
| 6,744,824 | B1 | 6/2004 | Duvaut et al. |
| 6,752,768 | B2 | 6/2004 | Burdorff et al. |
| 6,863,676 | B2 | 3/2005 | Lee et al. |
| 6,923,754 | B2 | 8/2005 | Lubock |
| 6,945,942 | B2 | 9/2005 | Van Bladel et al. |
| 6,951,611 | B2 | 10/2005 | Dannenmaier et al. |
| 6,955,641 | B2 | 10/2005 | Lubock |
| 7,041,217 | B1 | 5/2006 | Close et al. |
| 7,044,957 | B2 | 5/2006 | Foerster et al. |
| 7,066,893 | B2 | 6/2006 | Hibner et al. |
| 7,226,424 | B2 | 6/2007 | Ritchart et al. |
| 7,276,032 | B2 | 10/2007 | Hibner |
| 7,316,726 | B2 | 1/2008 | Schwindt |
| 7,351,210 | B2 | 4/2008 | Cicenas et al. |
| 7,442,171 | B2 | 10/2008 | Stephens et al. |
| 7,611,474 | B2 | 11/2009 | Hibner et al. |
| 2001/0014785 | A1 | 8/2001 | Sussman et al. |
| 2001/0032649 | A1 | 10/2001 | Nagano |
| 2002/0016544 | A1 | 2/2002 | Hareyama et al. |
| 2002/0082518 | A1* | 6/2002 | Weiss et al. ............... 600/566 |
| 2002/0082519 | A1 | 6/2002 | Miller et al. |
| 2002/0099307 | A1 | 7/2002 | Krause et al. |
| 2002/0120212 | A1 | 8/2002 | Ritchart et al. |
| 2003/0018281 | A1 | 1/2003 | Huitema |
| 2003/0073929 | A1 | 4/2003 | Baltschun et al. |
| 2003/0097079 | A1 | 5/2003 | Garcia |
| 2003/0109801 | A1 | 6/2003 | Rhad et al. |
| 2003/0109803 | A1 | 6/2003 | Huitema et al. |
| 2003/0195436 | A1 | 10/2003 | Van Bladel et al. |
| 2003/0199753 | A1 | 10/2003 | Hibner et al. |
| 2003/0199754 | A1 | 10/2003 | Hibner et al. |
| 2003/0199785 | A1 | 10/2003 | Hibner et al. |
| 2003/0199787 | A1 | 10/2003 | Schwindt |
| 2003/0216667 | A1 | 11/2003 | Viola |
| 2003/0233054 | A1 | 12/2003 | Stephens et al. |
| 2004/0034280 | A1 | 2/2004 | Privitera et al. |
| 2004/0049128 | A1 | 3/2004 | Miller et al. |
| 2004/0077938 | A1 | 4/2004 | Mark et al. |
| 2004/0077972 | A1 | 4/2004 | Tsonton et al. |
| 2004/0158207 | A1 | 8/2004 | Hunn et al. |
| 2004/0162505 | A1* | 8/2004 | Kaplan et al. ............... 600/567 |
| 2004/0210161 | A1 | 10/2004 | Burdorff et al. |
| 2004/0222137 | A1 | 11/2004 | Hashimoto |
| 2004/0222145 | A1 | 11/2004 | Onoue et al. |
| 2004/0230133 | A1 | 11/2004 | Miller et al. |
| 2005/0027210 | A1* | 2/2005 | Miller ............... 600/567 |
| 2005/0049521 | A1 | 3/2005 | Miller et al. |
| 2005/0065453 | A1* | 3/2005 | Shabaz et al. ............... 600/564 |
| 2005/0101880 | A1* | 5/2005 | Cicenas et al. ............... 600/567 |
| 2005/0113715 | A1 | 5/2005 | Schwindt et al. |
| 2005/0212175 | A1 | 9/2005 | Tsonton et al. |
| 2005/0215922 | A1 | 9/2005 | Tsonton et al. |
| 2005/0240074 | A1 | 10/2005 | Lubock |
| 2005/0261581 | A1 | 11/2005 | Hughes et al. |
| 2005/0277829 | A1 | 12/2005 | Tsonton et al. |
| 2006/0009712 | A1 | 1/2006 | Van Bladel et al. |
| 2006/0074346 | A1 | 4/2006 | Hibner |
| 2006/0129063 | A1* | 6/2006 | Thompson et al. ............... 600/566 |
| 2006/0155209 | A1 | 7/2006 | Miller et al. |
| 2006/0155210 | A1 | 7/2006 | Beckman et al. |
| 2006/0235436 | A1 | 10/2006 | Anderson et al. |
| 2007/0038144 | A1 | 2/2007 | Hughes et al. |
| 2007/0118048 | A1 | 5/2007 | Stephens et al. |
| 2008/0033454 | A1 | 2/2008 | Lukoschek et al. |
| 2008/0103413 | A1 | 5/2008 | Cicenas et al. |
| 2008/0200835 | A1 | 8/2008 | Monson et al. |
| 2008/0300506 | A1* | 12/2008 | McIntyre ............... 600/566 |
| 2010/0057099 | A1 | 3/2010 | Fujimoto et al. |

FOREIGN PATENT DOCUMENTS

| | | |
|---|---|---|
| EP | 0161606 | 11/1985 |
| EP | 378692 | 7/1990 |
| EP | 0541970 | 5/1993 |
| EP | 1 604 615 A1 | 12/2005 |
| GB | 1252170 | 11/1971 |
| GB | 2018601 | 10/1979 |
| WO | WO-9008508 | 8/1990 |
| WO | WO-9314707 | 8/1993 |
| WO | WO-9525465 | 9/1995 |
| WO | WO-9632067 | 10/1996 |
| WO | WO-9724991 | 7/1997 |
| WO | WO-9806338 | 2/1998 |
| WO | WO-98/22022 A1 | 5/1998 |
| WO | WO-9825556 | 6/1998 |
| WO | WO-9855016 | 12/1998 |
| WO | WO-0149184 A2 | 7/2001 |
| WO | WO-01/54763 A2 | 8/2001 |
| WO | WO-01/82810 | 11/2001 |
| WO | WO-0197702 | 12/2001 |
| WO | WO-2004/043531 | 5/2004 |

OTHER PUBLICATIONS

Final Office Action dated Mar. 24, 2009 for U.S. Appl. No. 12/020,294.

Response to Office Action dated Sep. 3, 2009 for U.S. Appl. No. 12/020,294.

Amendment to Office Action dated Oct. 27, 2008 to U.S. Appl. No. 12/031,423.

Amendment to Office Action dated Oct. 2, 2008 for U.S. Appl. No. 12/020,294.

Amendment in response to Final Office Action dated Mar. 24, 2009 for U.S. Appl. No. 12/020,294.

Amendment in Response to Final Office Action dated Feb. 27, 2009 for U.S. Appl. No. 12/031,423.

Office Action dated Sep. 3, 2009 for U.S. Appl. No. 12/020,294.

Office Action dated Jul. 8, 2009 for U.S. Appl. No. 12/031,423.

Response to Office Action dated Jul. 8, 2009 for U.S. Appl. No. 12/031,423.

PCT International Search Report for PCT/US2008/077841 dated Oct. 5, 2009.
Final Office Action dated Jan. 8, 2010 for U.S. Appl. No. 12/031,423.
Response to Final Office Action dated Jan. 8, 2010 for U.S. Appl. No. 12/031,423.
Complaint for case *Ethicon Endo-Surgery, INc.* v. *Hologic, Inc., et al.*; U.S. District Court of Delware Case No. 09-580 (JJF) dated Aug. 6, 2009.
Defendant Hologic, Inc. et al's. Answer and Counterclaims for *Ethicon Endo-Surgery, Inc.* v. *Hologic, Inc. et al*; U.S. District Court of Delaware Case No. 09-580 (JJF) dated Aug. 27, 2009.
Answer to Counterclaims for *Ethicon Endo-Surgery, Inc.* v. *Hologic, Inc. et al.*; U.S. District Court of Delaware Case No. 09-580 (JJF) dated Sep. 7, 2009.
Final Office Action dated Mar. 29, 2010 for U.S. Appl. No. 12/020,294.
Non-Final Office Aciton dated Aug. 27, 2010 for U.S. Appl. No. 12/020,294.
Response to Final Office Action dated Mar. 29, 2010 for U.S. Appl. No. 12/020,294.
Non-Final Office Action dated Oct. 25, 2010 for U.S. Appl. No. 11/875,560.
Response to Non-Final Office Action dated Aug. 27, 2010 for U.S. Appl. No. 12/020,294.
Non-Final Office Action dated Jan. 14, 2011 for U.S. Appl. No. 12/031,423.
Response to Non-Final Office Action dated Oct. 25, 2010 for U.S. Appl. No. 11/875,560.
Final Office Action dated Feb. 1, 2011 for U.S. Appl. No. 12/020,294.
Final Office Action dated Mar. 25, 2011 for U.S. Appl. No. 11/875,560.
Response to Non-Final Office Action dated Jan. 14, 2011 for U.S. Appl. No. 12/031,423.
Response to Final Office Action dated Feb. 1, 2011 for U.S. Appl. No. 12/020,294.
Final Office Action dated Apr. 27, 2011 for U.S. Appl. No. 12/031,423.
Response to Final Office Action dated Mar. 25, 2011 for U.S. Appl. No. 11/875,560.
Response to Final Office Action dated Apr. 27, 2011 for U.S. Appl. No. 12/031,423.
Non-Final Office Action dated Jul. 20, 2011 for U.S. Appl. No. 12/020,294.
International Search Report No. PCT/US01/51235 dated Dec. 10, 2002.
Publication in Design News entitled "Probe reduces breast biopsy trauma" by Joseph Ogando dated Aug. 7, 2000.
Steven K. Wagner, "Imaging News," Breast ultrasound spurs biopsy technology race, (Mar. 6, 1996).
International Search Report No. PCT/IB2006/051585 dated Aug. 30, 2006.
International Search Report #PCT/US03/26958 dated Apr. 2, 2004.
Reuters Heatlh publication entitled "Contrast mammography shows promise in cancer detection." author David Douglas, Oct. 2003.
Aunt Minnie.com publication entitled "TechniScan system completes phase I trials.", Jan. 2003.
MSNBC Heath Publication entitled "Seeds may zap breast cancer." Author Robert Bazell, May 2001.
Radiology Today—Technology Trends, article entitled "New Use for an Old Technology Applying Tomosynthesis to Mammography." Author Dan Harvey, Apr. 26, 2004.
Biophontonics International—Imaging article entitled "Optoacoustics Moves Closer to the Clinic." Author Nadya Anscombe, Apr. 2003.
PCT International Search Report #PCT/IB2006/053504 dated Apr. 2, 2007.
International Search Report PCT/US207/061910 dated Nov. 6, 2007.
WebMd Medical Dictiionary "What is Tissue?" 2006, http://dictionary.webmd.com/terms/tissue.xml.
blood: definition, usage and pronunciation, YourDictionary.com, http://www.yourdictionary.com/blood, Jan. 21, 2008.
Blood-definnition from Biology-Online.org, Oct. 3, 2005, http://www.biology-online.org/dictionary/Blood.
Eionet GEMET Thesaurus, "blood (tissue)", Oct. 17, 2007, http://www.eionet.europa.eu/gemet/concept?cp=935.
Biology 20-Investigation "Blood Tissue", www.blackgold.ab.ca/microtest/Biology 20 Labs/blood_tissue.pdf.
Parker & Klaus, "Performing a Breast Biopsy with a Directional, Vacuum-assisted Biopsy Instrument," *RadioGraphics* 17(5):1233-1252 (1997).
Burbank, "Stereotactic Breast Biopsy: Its History, Its Present, and Its Future," *The American Surgeon* 62:128-50 (1996).
Parker & Burbank, "A Practical Approach to Minimally Invasive Breast Biopsy," *Radiology* 200:11-20 (1996).
Burbank, "Stereotactic Breast Biopsy of Atypical Ductal Hyperplasia and Ductal Carcinoma in Situ Lesions: Improved Accuracy with Directional, Vacuum-Assisted Biopsy," *Radiology* 202: 843-47 (1997).
Parker, Dennis, & Stavros, "Critical Pathways in Percutaneous Breast Intervention," *Imaging Symposium* 15(4) 1995.
Parker, Lovin, Jobe, Luethke, Hopper, Yakes, Burke, "Stereotactic Breast Biopsy with a Biopsy Gun," *Radiology* 176:741-47 (1990).
Office Action dated Oct. 2, 2008 in U.S. Appl. No. 12/020,294.
Office Action dated Oct. 27, 2008 in U.S. Appl. No. 12/031,423.
Non-Final Office Action dated Sep. 29, 2011 for U.S. Appl. No. 12/031,423.
Response to Non-Final Office Action dated Jul. 20, 2011 for U.S. Appl. No. 12/020,294.
Non-Final Office Action dated Oct. 25, 2011 for U.S. Appl. No. 11/875,560.
Final Office Action dated Nov. 9, 2011 for U.S. Appl. No. 12/020,294.

* cited by examiner

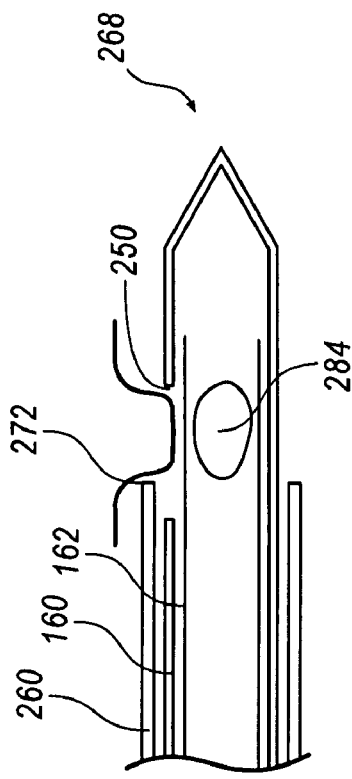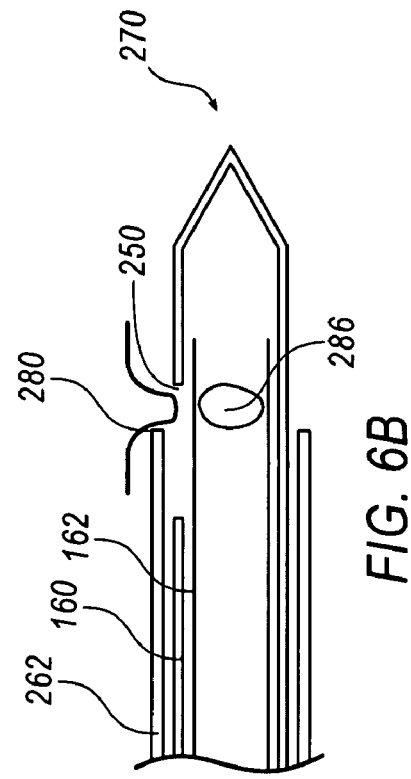
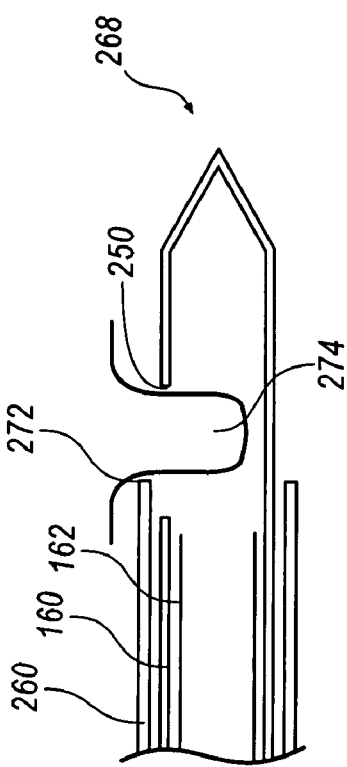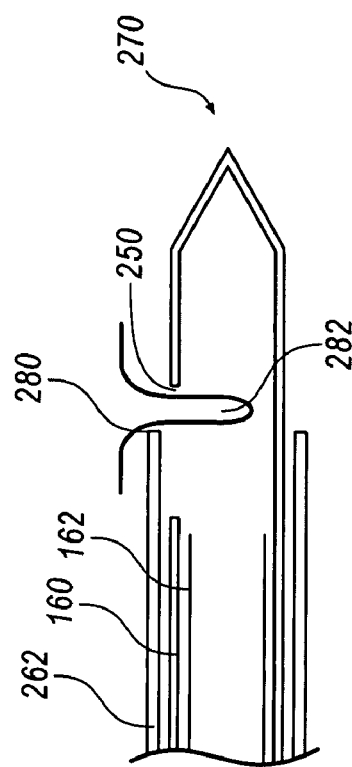
FIG. 6A
FIG. 6B

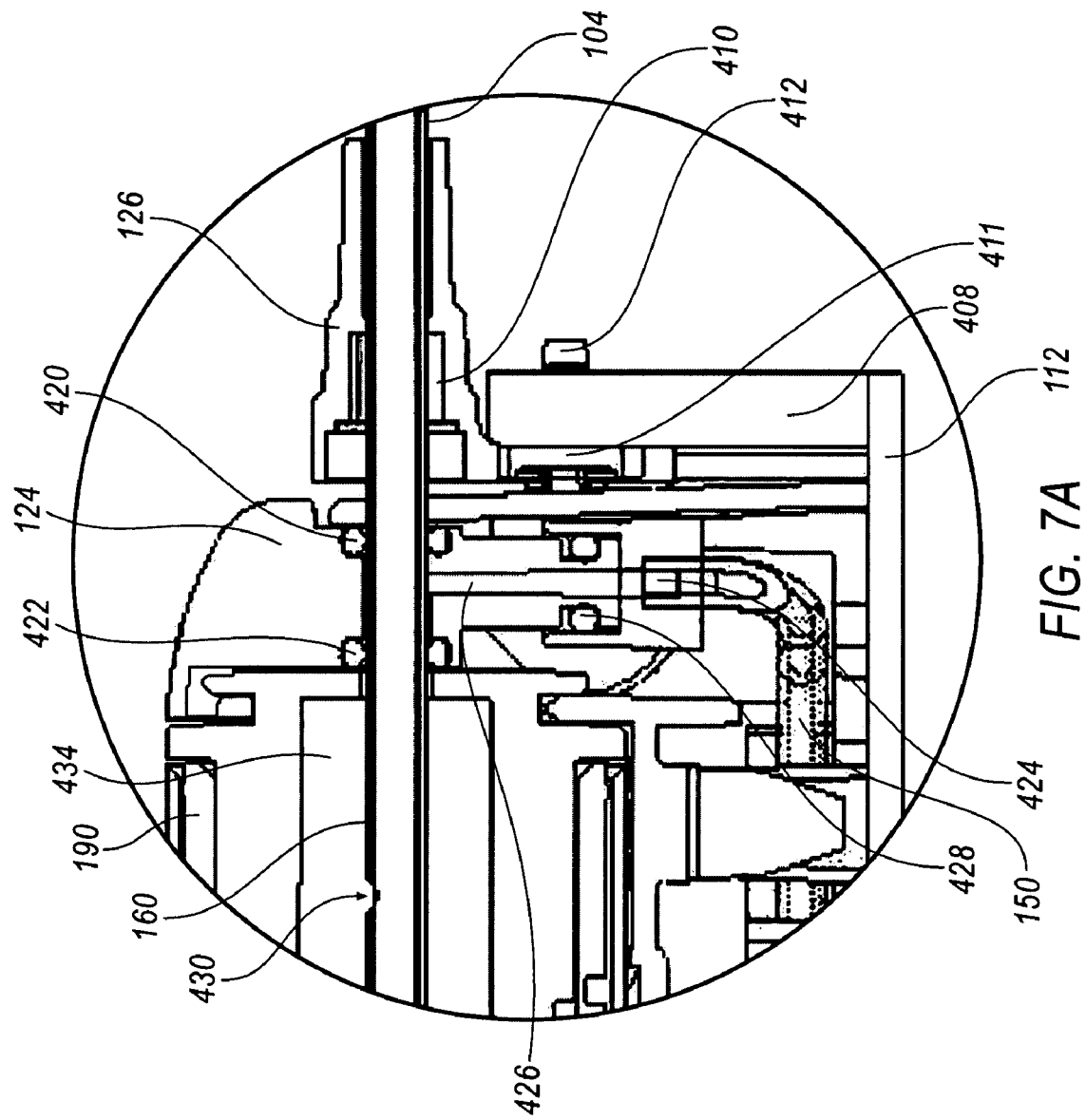

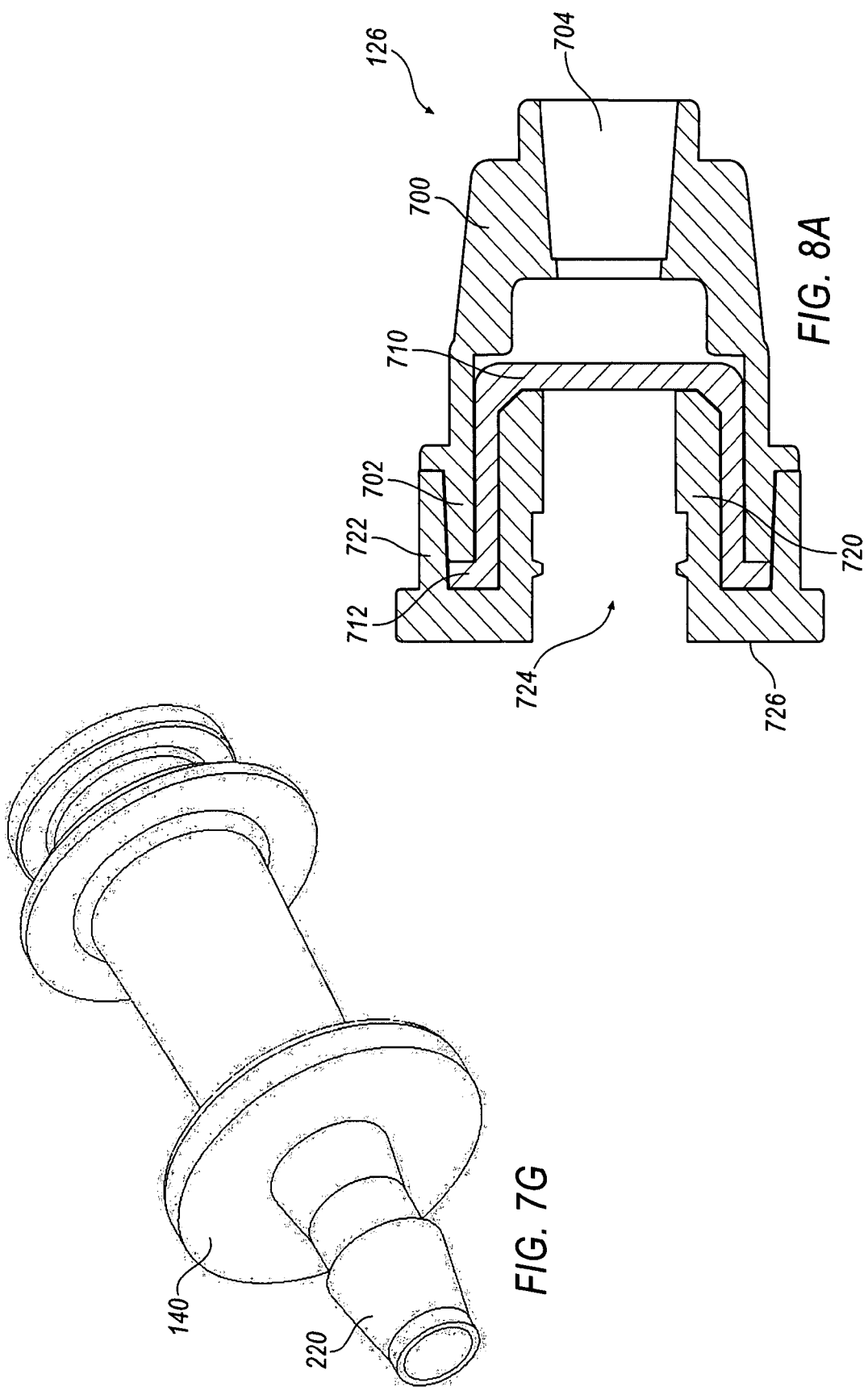

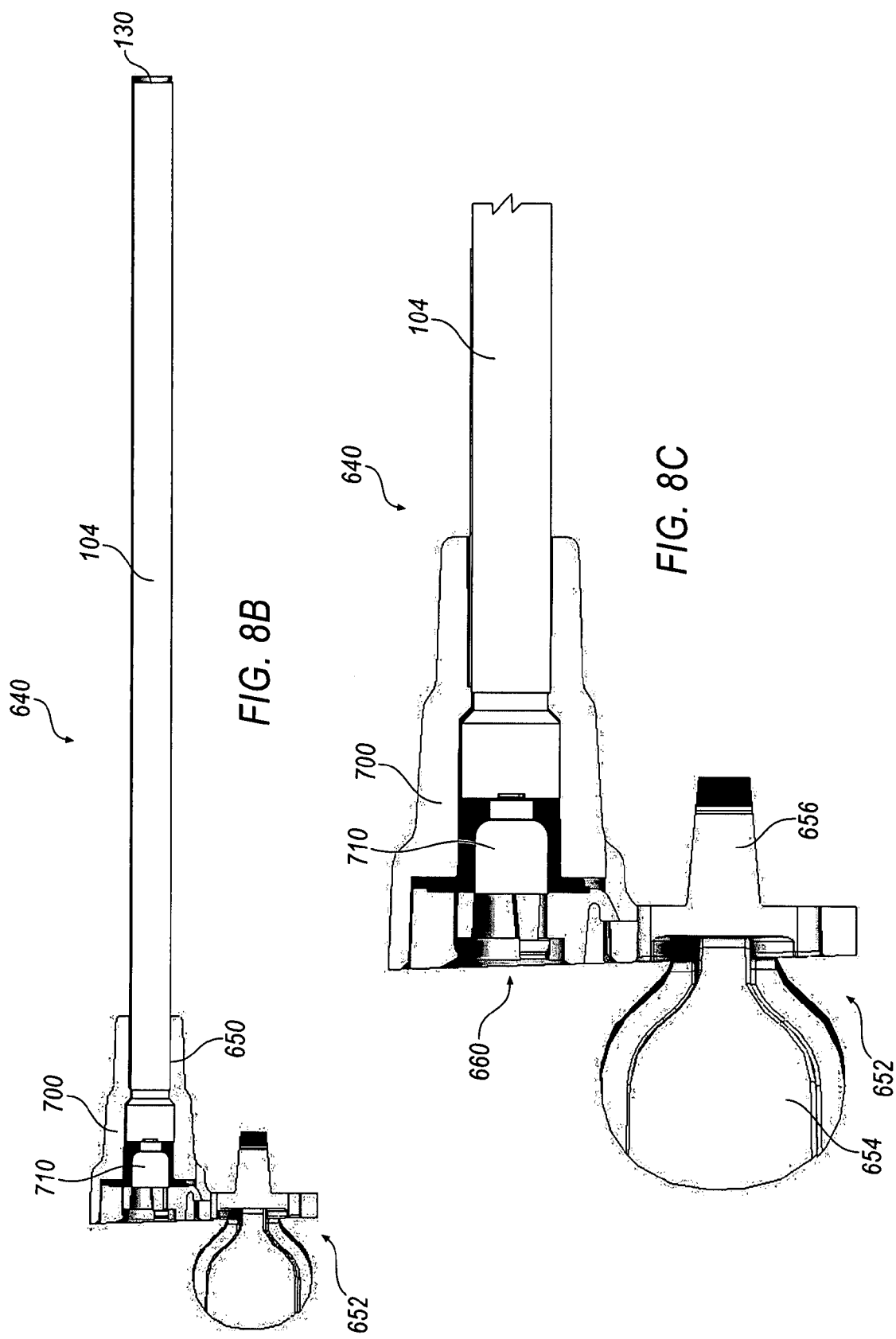

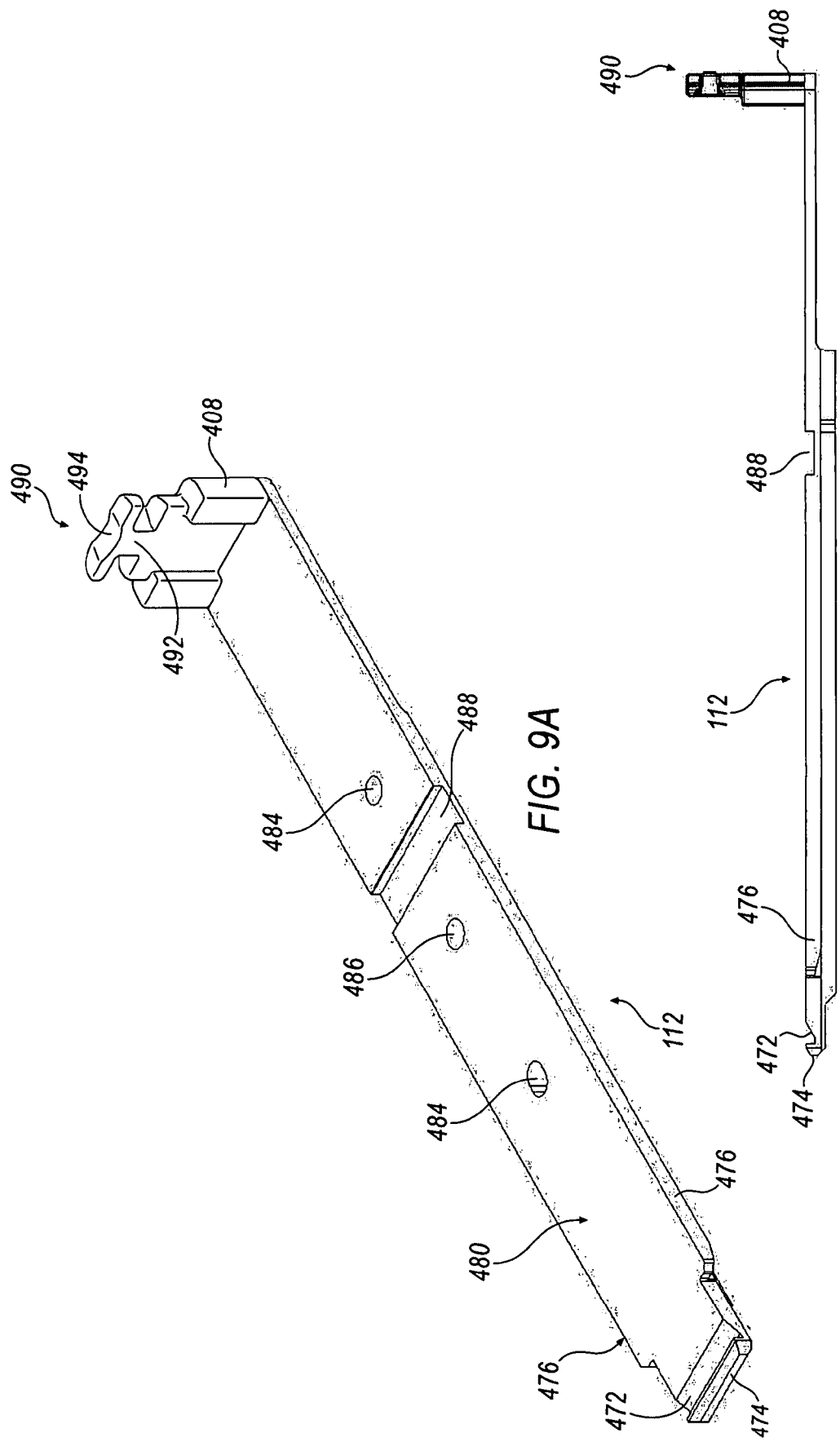

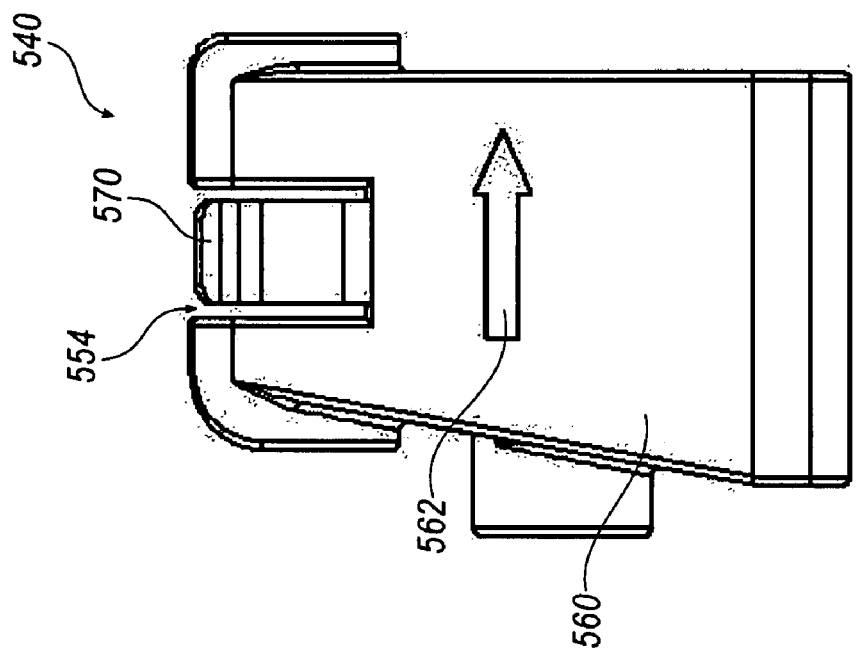
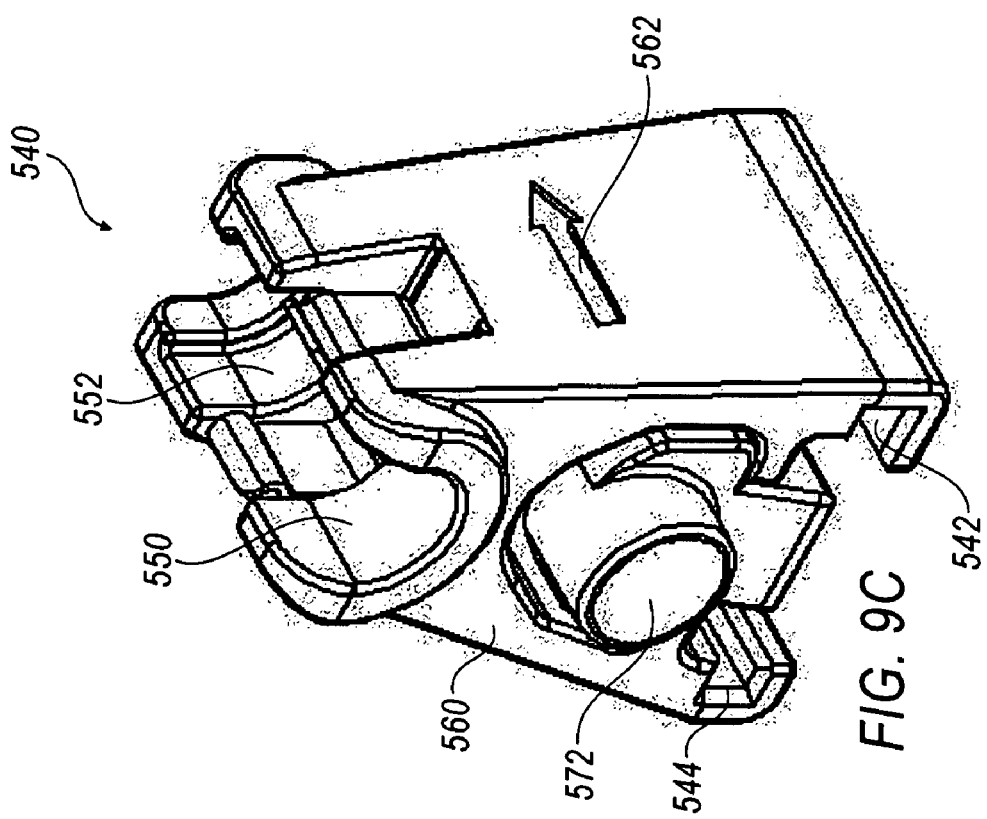

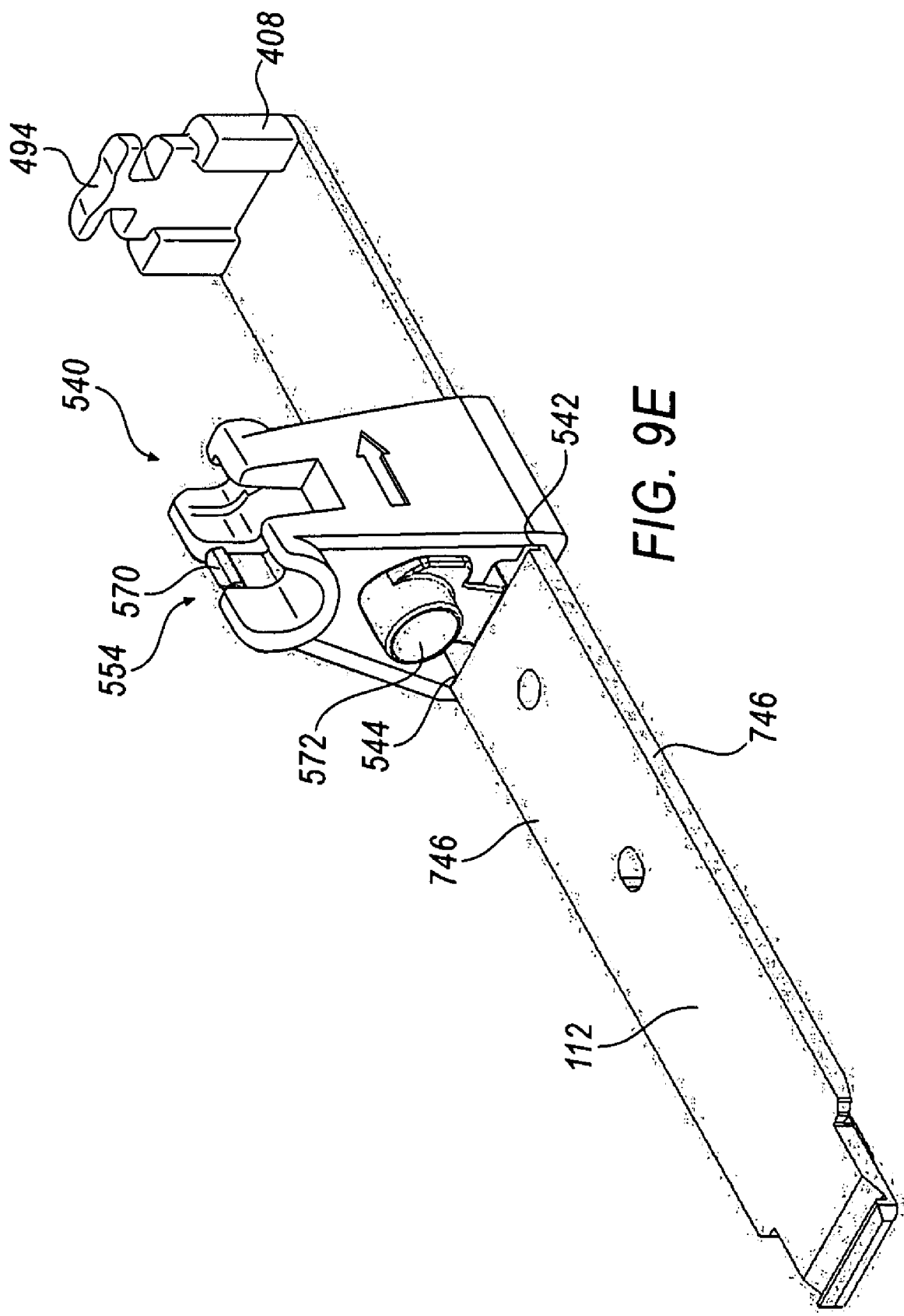

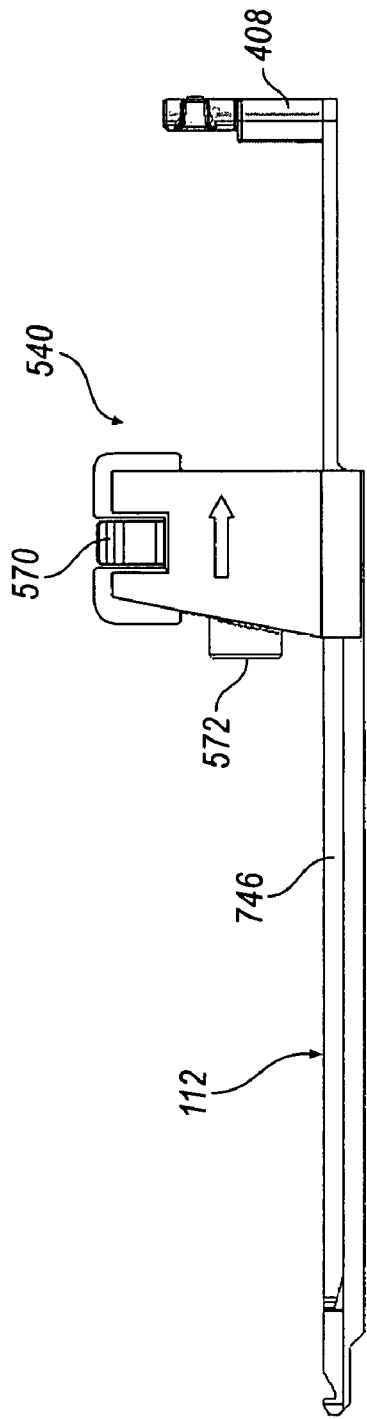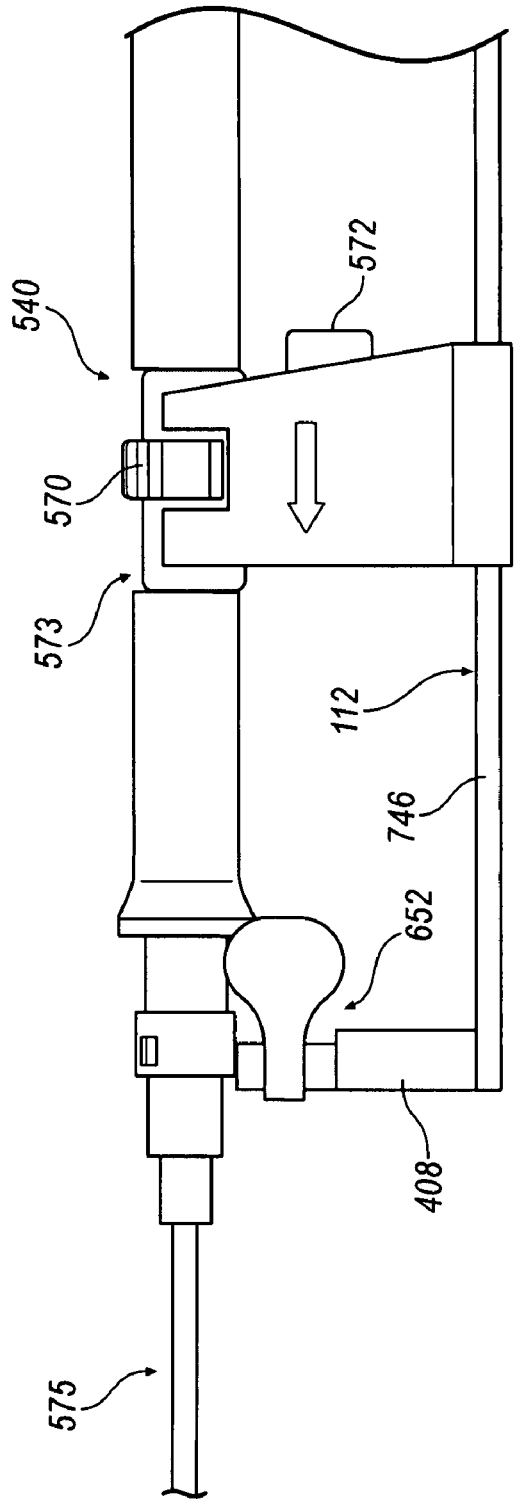

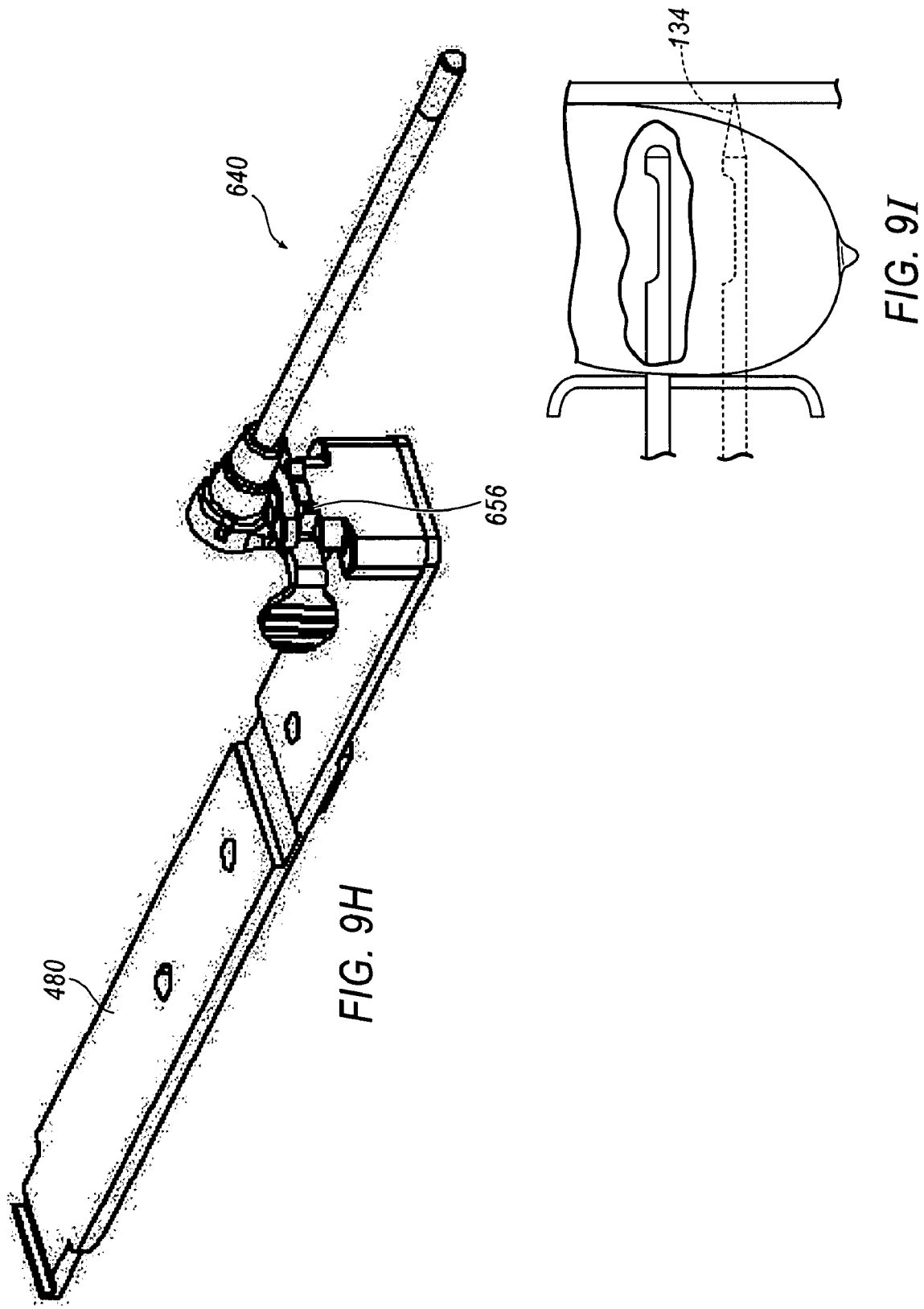

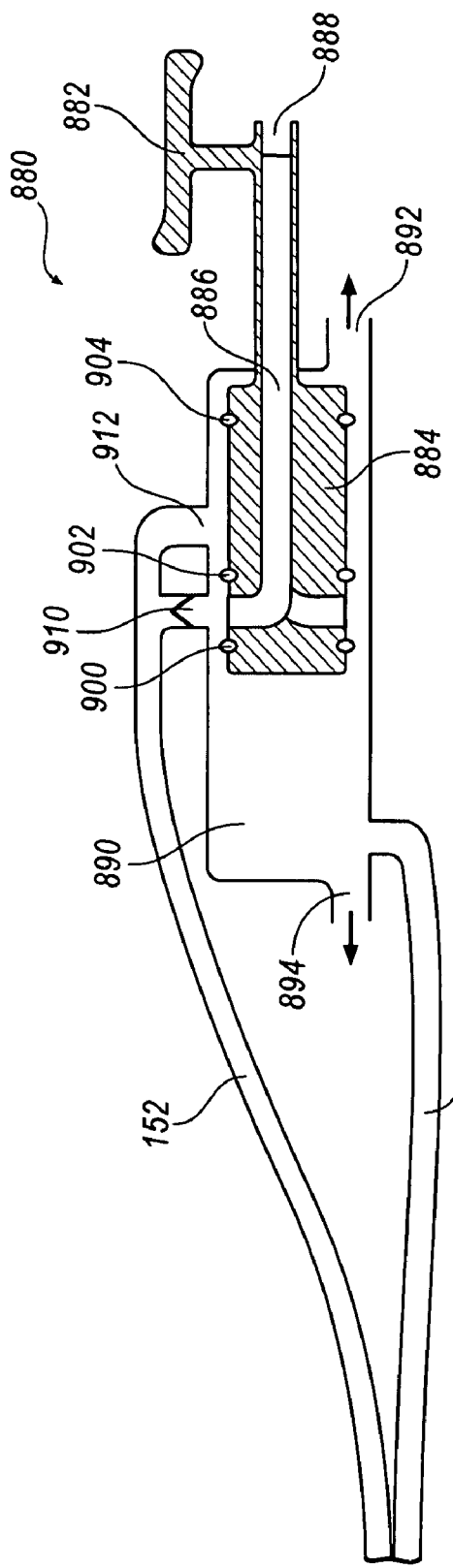
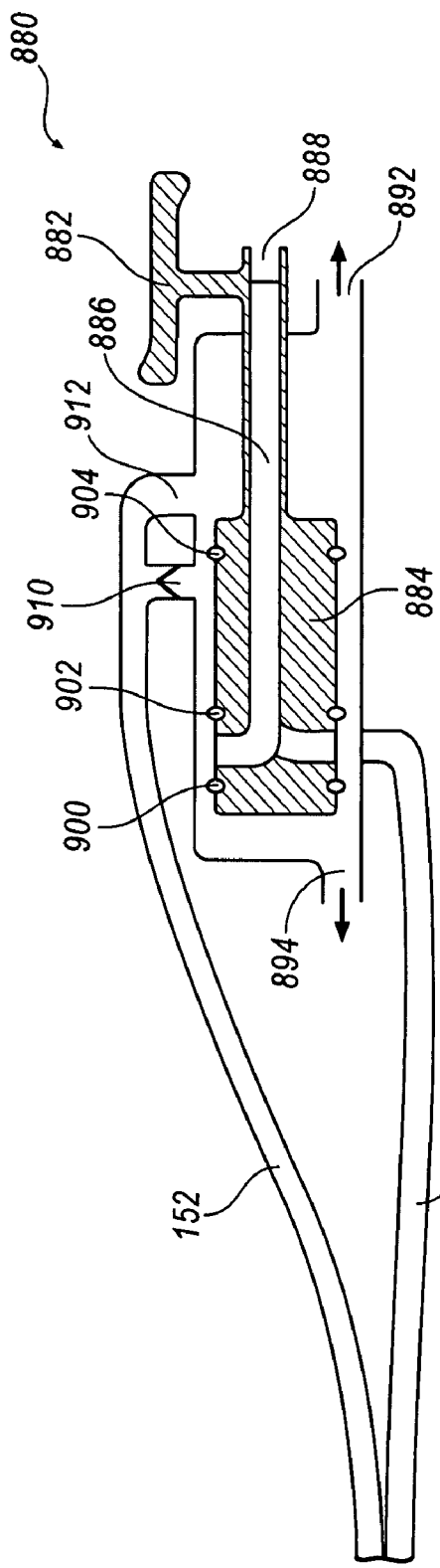
FIG. 13A
FIG. 13B

SURGICAL DEVICE

FIELD

This disclosure relates to biopsy instruments and methods for taking a biopsy. More specifically, this disclosure relates to disposable biopsy devices for removing several tissue samples using a single insertion.

BACKGROUND INFORMATION

In the diagnosis and treatment of breast cancer, it is often necessary to remove multiple tissue samples from a suspicious mass. The suspicious mass is typically discovered during a preliminary examination involving visual examination, palpitation, X-ray, MRI, ultrasound imaging or other detection means. When this preliminary examination reveals a suspicious mass, the mass must be evaluated by taking a biopsy in order to determine whether the mass is malignant or benign. Early diagnosis of breast cancer, as well as other forms of cancer, can prevent the spread of cancerous cells to other parts of the body and ultimately prevent fatal results.

A biopsy of the breast, for example, can be performed by either an open procedure or a percutaneous method. The open surgical biopsy procedure first requires localization of the lesion by insertion of a wire loop, while using a visualization technique, such as X-ray or ultrasound. Next, the patient is taken to a surgical room where a large incision is made in the breast, and the tissue surrounding the wire loop is removed. This procedure causes significant trauma to the breast tissue, often leaving disfiguring results and requiring considerable recovery time for the patient. This is often a deterrent to patients receiving the medical care they require. The open technique, as compared to the percutaneous method, presents increased risk of infection and bleeding at the sample site. Due to these disadvantages, percutaneous methods are often preferred.

Percutaneous biopsies have been performed using either fine needle aspiration or core biopsy in conjunction with real-time visualization techniques, such as ultrasound, mammography (X-ray), MRI, PET, CT, terahertz technologies, etc. Fine needle aspiration involves the removal of a small number of cells using an aspiration needle. A smear of the cells is then analyzed using cytology techniques. Although fine needle aspiration is less intrusive than an open procedure, only a small amount of cells are available for analysis. In addition, this method does not provide for a pathological assessment of the tissue, which can provide a more complete assessment of the stage of the cancer, if found. In contrast, in core biopsy a larger fragment of tissue can be removed without destroying the structure of the tissue. Consequently, core biopsy samples can be analyzed using a more comprehensive histology technique, which indicates the stage of the cancer. In the case of small lesions, the entire mass may be removed using the core biopsy method. For these reasons core biopsy is preferred, and there has been a trend towards the core biopsy method, so that a more detailed picture can be constructed by pathology of the disease's progress and type.

The first core biopsy devices were of the spring advanced, "Tru-Cut" style consisting of a hollow tube with a sharpened edge that was inserted into the breast to obtain a plug of tissue. This device presented several disadvantages. First, the device would sometimes fail to remove a sample, therefore, requiring additional insertions. This was generally due to tissue failing to prolapse into the sampling notch. Secondly, the device had to be inserted and withdrawn to obtain each sample, therefore, requiring several insertions in order to acquire sufficient tissue for pathology.

Vacuum assisted core biopsy devices were subsequently developed that required only a single insertion into the biopsy site to remove multiple tissue samples. An example of a vacuum assisted core biopsy device incorporates a tube within a tube design that includes an outer piercing needle having a sharpened end for piecing the tissue. The outer tube has an opening for receiving tissue. An inner tube is slidingly disposed within the outer tube, and serves to cut tissue that has prolapsed into the opening in the outer cannula. A vacuum is used to draw the tissue into the opening in the outer cannula.

Vacuum assisted core biopsy devices are available in handheld (for use with ultrasound) and stereotactic (for use with X-ray) versions. Stereotactic devices are mounted to a stereotactic unit that locates the lesion and positions the needle for insertion. In preparation for a biopsy using a stereotactic device, the patient lies face down on a table and the breast protrudes from an opening in the table. The breast is then compressed and immobilized by two mammography plates. The mammography plates create images that are communicated in real-time to the stereotactic unit. The stereotactic unit then signals the biopsy device and positions the device for insertion into the lesion by the operator.

In contrast, when using the handheld model, the breast is not immobilized. Rather the patient lies on her back and the doctor uses an ultrasound device to locate the lesion. The doctor must then simultaneously operate the handheld biopsy device and the ultrasound device.

While the vacuum assisted core biopsy device presented an advancement in the field of biopsy devices, several disadvantages remain with some of the currently marketed devices. For example, when using the current biopsy devices, physicians have encountered significant difficulties severing the tissue. For instance, the inner cutter often fails to completely sever the tissue. When the inner cutting needle is withdrawn, no tissue sample is present (dry tap), and therefore, reinsertion is required. In the case of the vacuum assisted core biopsy device described above, the failure to completely sever the tissue after the first advancement of the inner cutter results in a necessary second advancement of the inner cutter. In this event, the procedure is prolonged, which is significant because the amount of trauma to the tissue and, ultimately, to the patient is greatly affected by the length of the procedure. Therefore, it is in the patient's best interest to minimize the length of the procedure by making each and every attempt at cutting the tissue a successful and complete cut.

In light of the foregoing disadvantages, a need remains for a tissue removal device that reliably applies a vacuum without becoming plugged with blood and bodily fluids. A need also remains for a tissue removal device that is entirely disposable so that both exposure to bio-hazard and clean-up time are significantly minimized, while convenience is maximized. A further need remains for a tissue removal device that completely severs the maximum amount of tissue without requiring numerous attempts at cutting the tissue. A need also remains for a tissue removal device that is compatible with multiple imaging modalities. Finally, a need remains for a biopsy tissue removal device that is easy to use and does not cause a surgeon strain during use, but provides satisfactory access to a lesion to be biopsied.

BRIEF SUMMARY

A surgical device is disclosed. The surgical device comprises an outer sleeve, a cutting element, a spool, a piston, and a spring. The cutting element extends from the outer sleeve at the distal end of the outer sleeve. The cutting element comprises an outer cannula and an inner cannula. The spool is engaged with the outer cannula. The piston is engaged with the inner cannula. A spring is positioned between the spool and the piston. The spool is translated distally to translate the outer cannula towards the distal end. And the piston translates the inner cannula towards the distal end to sever tissue.

BRIEF DESCRIPTION OF THE DRAWINGS

These and other features and advantages of the invention will be apparent from the following detailed description and the appended claims, taken in conjunction with the accompanying drawings, in which:

FIG. 1A is a schematic view of a surgical system for use with the surgical device of FIG. 1.

FIG. 1B is an enlarged view of an alternative embodiment of a distal end of the surgical device of FIG. 1.

FIG. 6A shows cross-sectional views of tissue prolapsed through a sampling aperture formed in the outer cannula shown in FIG. 4 using different length introducer cannulas.

FIG. 6B shows cross-sectional views of resected tissue using different length introducer cannulas.

FIG. 7A is a partial enlarged cross-sectional view of the front of the surgical device taken from encircled area 7A of FIG. 7

FIG. 7G is a perspective view of a vacuum attachment for use with the rotator of FIG. 7E.

FIG. 8A is a cross-sectional view of an introducer hub.

FIG. 8B is a cross-sectional view of an introducer system for use with the surgical device of FIG. 1.

FIG. 8C is a partial cross-sectional view of an introducer system, an introducer cannula and an introducer hub.

FIG. 9A is a perspective view of an adapter for use with the surgical device of FIG. 1.

FIG. 9B is a side view of the adapter of FIG. 9A.

FIG. 9C is a perspective view of a trocar holder for use with the surgical device of FIG. 1.

FIG. 9D is a side view of the trocar holder of FIG. 9C.

FIG. 9E is a perspective view of the trocar holder of FIG. 9C and the adapter of FIG. 9A.

FIG. 9F is a side view of the trocar holder and the adapter of FIG. 9E.

FIG. 9G is a side view of the trocar holder and the adapter of FIG. 9E with a trocar positioned within the trocar holder.

FIG. 9H is a perspective view of an introducer attached to the adapter of FIG. 9A.

FIG. 9I is a side view of a breast in compression.

FIG. 13A is a cross-sectional view of an alternative embodiment of a remote valve in a cocked position.

FIG. 13B is a cross-sectional view of an alternative embodiment of a remote valve in a fired position.

DETAILED DESCRIPTION OF THE EMBODIMENTS

Figure 1:
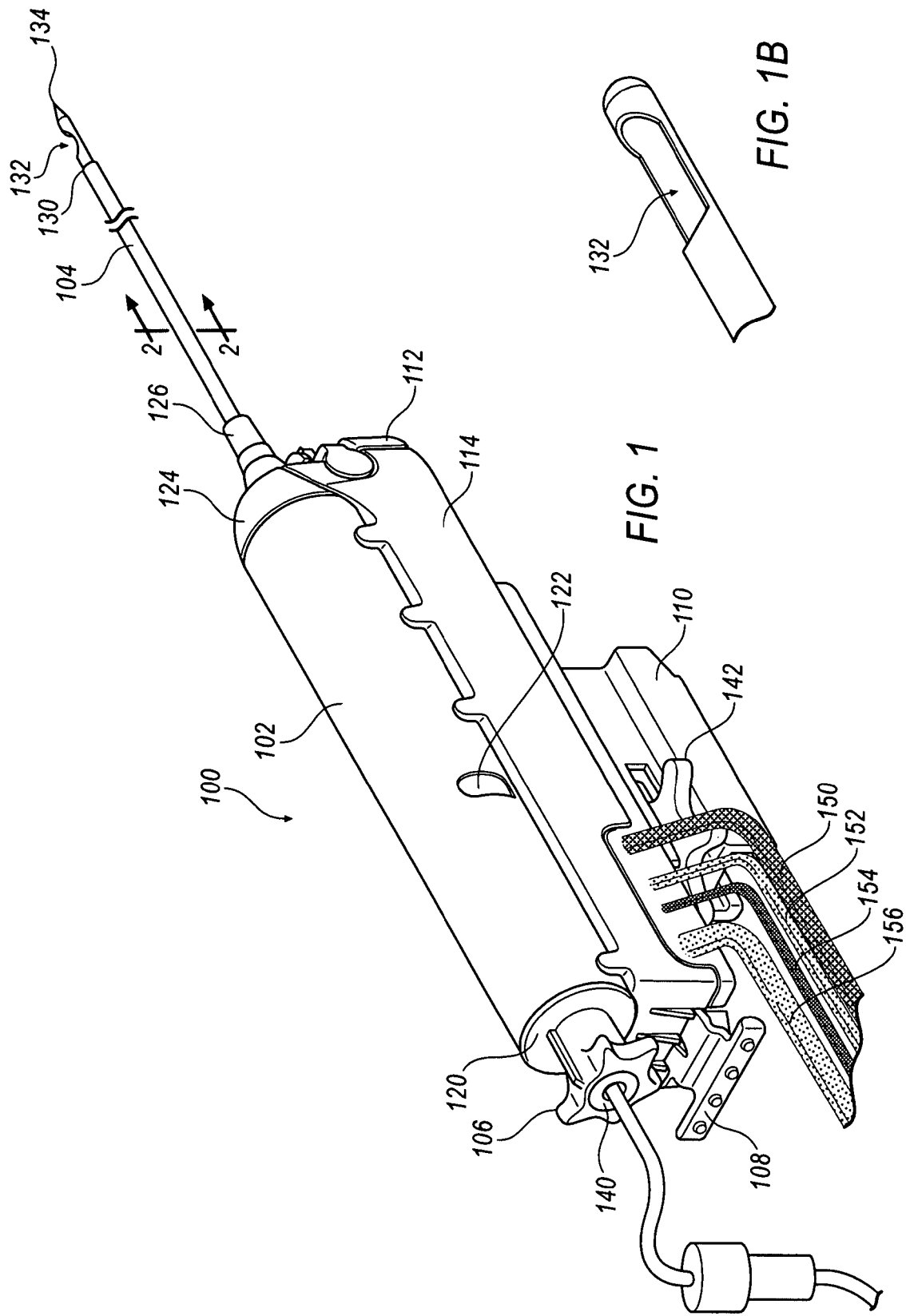
FIG. 1 is a perspective view of a surgical device, according to a representative embodiment of the disclosure.

Referring to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Overview

A tissue removal device used for breast biopsy is attached to a stereotactic table for positioning. A patient's target area for tissue removal is immobilized (e.g., a breast) in relation to the tissue removal device. The stereotactic table allows precise positioning of a biopsy device, or any other device, at a known target area. Moreover, the stereotactic table allows for visualization of a known location for confirmation or for providing a three-dimensional location future analysis and/or treatment. In many cases, the tissue removal device is a surgical device, such as is described in detail below and in the drawings.

The device may include an adapter for mounting the surgical device to a positioning system, for example, a stereotactic table. However, the surgical device may also be used with other positioning systems. In such a case, the adapter may be configured to engage both the positioning system and the surgical device. In an example, a Lorad® bracket may be used to attach the device to a Lorad® table.

When the surgical device is installed with a positioning system, movements of the positioning system allow for the precise removal of tissue samples. Moreover, a surgeon may use one or many visualization systems (i.e., imaging modalities) to further identify a target area and then precisely position the surgical device to remove tissue at the target area. The imaging modalities include, for example, MRI, PET, CT, ultrasound, terahertz technologies, etc. The location of the target area is determined and the position is recorded for manual or automatic movement of the positioning system and the surgical device.

An introducer cannula is positioned and inserted into the patient to provide a pathway to the target location, in one example using a separate "stylet" to pierce the patient's tissue. The stylet, which is inserted through the introducer cannula and moved into the patient with the introducer cannula, is removed from the introducer cannula after creating the pathway. The surgical device is then inserted through the introducer cannula and into the pathway to the target site. Once the surgical device is positioned, the tissue cutting portion of the device that is part of the surgical device is thereby positioned within the patient close to the target site. In a blunt tip embodiment of the surgical device, once the surgical device is positioned within the pathway, the device is ready to resect tissue samples.

In another embodiment with a trocar tip, the introducer cannula may be disposed over an outer cannula of the surgical device. The trocar tip may be used to create the pathway for the surgical device. Alternatively, the stylet may also be used, as described above. Once the inserted into the patient, the tissue cutting portion is then fired to a final distance to the target site and tissue is resected (i.e., severed removed from the patient). The resected tissue may be used for diagnosis of the possible pathologic condition or tissue may be debulked to remove the target area in its entirety.

In use, for example, the surgical device may be activated by using remote valves. In another example, the surgical device is operated using a remote valve to fire the tissue cutting portion into the patient to the final position and a console pedal is used to perform the biopsy functions.

Before, during, or after tissue is removed, one or more treatments may also be introduced at the target site. Such treatments include brachytherapy and other adjuvant treatments (such as, ablating tissue, heating tissue, freezing tissue, applying chemicals to tissue, external beam HIFU therapy, interstitial HIFU therapy, electroporation therapy, ultrasonicporation therapy, interstitial microwave therapy, etc.). Examples of such adjuvant treatments are described in co-pending U.S. patent application Ser. No. 11/550,209, entitled "SYSTEM AND METHOD FOR MINIMALLY INVASIVE DISEASE THERAPY," filed Oct. 17, 2006 by Joseph L. Mark, the contents of which are included in their entirety herein.

Referring now to the drawings, FIG. 1 shows a surgical device 100. Surgical device 100 includes an outer sleeve 102, an introducer cannula 104, and a rotator 106. Further, surgical device 100 is positioned on a cradle top 114. An adapter 112 connects cradle top 114 to a bracket 110. In an embodiment, surgical device 100 including outer sleeve 102, introducer cannula 104, rotator 106, and cradle top 114 are disposable. Adapter 112 is positioned underneath surgical device 100 (explained in detail below with respect to FIGS. 7, 9a, and 9e) and is typically left attached to a positioning table for reuse with another surgical device 100. A latch lever 108 is operable to release cradle top 114 from adapter 112. Outer sleeve 102 is provided to hold moving components and seals internal to surgical device 100 and between a proximal cap 120 and a front cap 124. Introducer cannula 104 is fixed to an introducer hub 126 that removably attaches cutting element 132 and adapter 112. During a procedure, introducer cannula 104 is positioned to allow for the insertion of surgical device 100 near the target site. When surgical device is positioned, a cutting element 132 protrudes (shown here in a fired position and explained below in detail with respect to FIG. 4) at a distal end 130 of introducer cannula 104. In one embodiment, cutting element 132 also includes a trocar tip 134 that is designed to easily penetrate tissue with minimal damage.

Alternatively, in one embodiment, cutting element 132 may include a blunt tip end (see FIG. 1B) that is not sharp (i.e., has a blunt tip). The blunt tip embodiment, which may include a generally hemispherical shape, is useful where the site of interest is close to the back plate of the compression device as the trocar tip may extend too far and exit the opposite side of the breast from the insertion point (as seen in FIG. 9I). Use of a cutting element 132 having a blunt tip end will be described in further detail below in connection with FIG. 9.

Referring now to FIG. 1A, a schematic view of a surgical system 192 for use with surgical device 100 is shown. Surgical system 192 includes a console 194, a remote valve 800, a user 196, and surgical device 100. User 196 is typically a surgeon and is able to control each of console 194, remote valve 800, and surgical device 100. Console 194 provides air pressure and vacuum, as well as control logic, to surgical device 100. Surgical device 100 is primarily controlled by user 196 at remote valve 800 during the high patient stress time of firing the cannula (for those embodiments with a trocar tip distal end), which is conveniently located between surgical device 100 and console 194.

Referring back to FIG. 1, a saline line 154, a firing line 152, a motor line 150, and a biopsy line 156 are attached to the surgical device. Lines 150-156 are also attached to a control console (not shown) for controlling surgical device 100. Cradle top 114 that receives, secures, and covers the internal attachment of saline line 154, firing line 152, motor line 150, and biopsy line 156. Cradle top 114 may be constructed of plastic or other suitable materials, in the representative embodiment shown, bracket 110 is configured as a "fisher" style bracket and attaches to adapter 112 by a screw. The shown bracket 110 is engaged or disengaged from a stereotactic table by rotating attachment wheel 142. It is appreciated, however, that the bracket 110 may be of other suitable configurations to permit use of the surgical device with other surgical tables.

Rotator 106 includes a fitting 140 where a vacuum line attaches to provide vacuum to cutting element 132. A rotation indicator 122 may be provided that describes the rotary position of cutting element 132. Rotation indicator 122 is a window that is cut through outer sleeve 102 so as to expose an inner body (see element 190 in FIG. 3) having indicia that rotates along with rotator 106. In general, when rotator 106 is turned by a user, the rotary position of cutting element 132 is shown by rotation indicator 122. Typically, a numeral is shown at rotation indicator 122 describing the position of cutting element 132 in a manner similar to a clock face. For example, the indicia of rotation indicator 122 may include numerals such as one (1) through twelve (12) o'clock. In this way, a surgeon can immediately and intuitively determine the rotary position of cutting element 132 by viewing rotation indicator 122. Moreover, rotation indicator 122 is highly visible and does not require special training to determine the angular position of cutting element 132. Alternatively, any indicia may be used for rotation indicator 122 to indicate the position of cutting element 132.

The components of surgical device 100 are configured such that the turning of rotator 106 is not overly burdensome on the operator (e.g., a surgeon). Thus, the torque required to turn rotator 106, and necessarily cutting element 132 including a sampling aperture 250 (see FIG. 4), is low. Thus, low grip strength and low torque is required to turn rotator 106 and cutting element 132. The low torque requirements are partially attributable to a floating o-ring design of the internal components (described below in detail with respect to FIG. 7D), a cup seal design or a combination of both.

Figure 2:
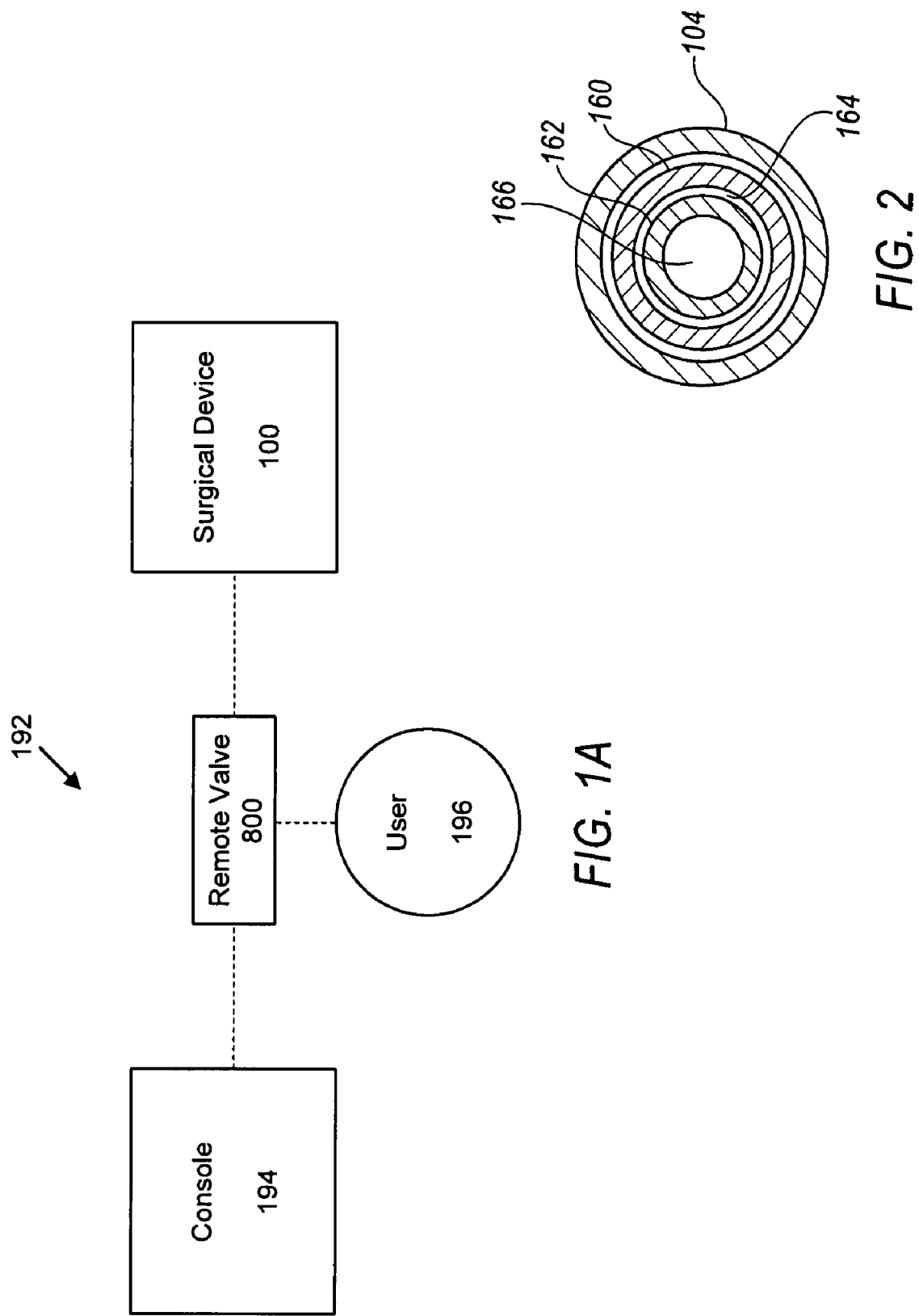
FIG. 2 is a cross-sectional view of a portion of the surgical device taken along lines 2-2 in FIG. 1.

FIG. 2 is a cross-sectional view of introducer cannula 104 taken along lines 2-2 of FIG. 1. As may be seen, an outer cannula 160 and an inner cannula 162 are disposed within introducer cannula 104. Cutting element 132 (see FIG. 1, and described below in detail with respect to FIG. 6) is a tube-within-a-tube arrangement that includes outer cannula 160 and inner cannula 162. When tissue is severed, a vacuum is pulled from inside inner cannula 162 at a sample lumen 166 where fluid and tissue are taken away and expelled at fitting 140 for collection in a tissue filter container. Moreover, saline or other therapeutics may be introduced to the target site through a gap 164 between outer cannula 160 and inner cannula 162.

Figure 3:
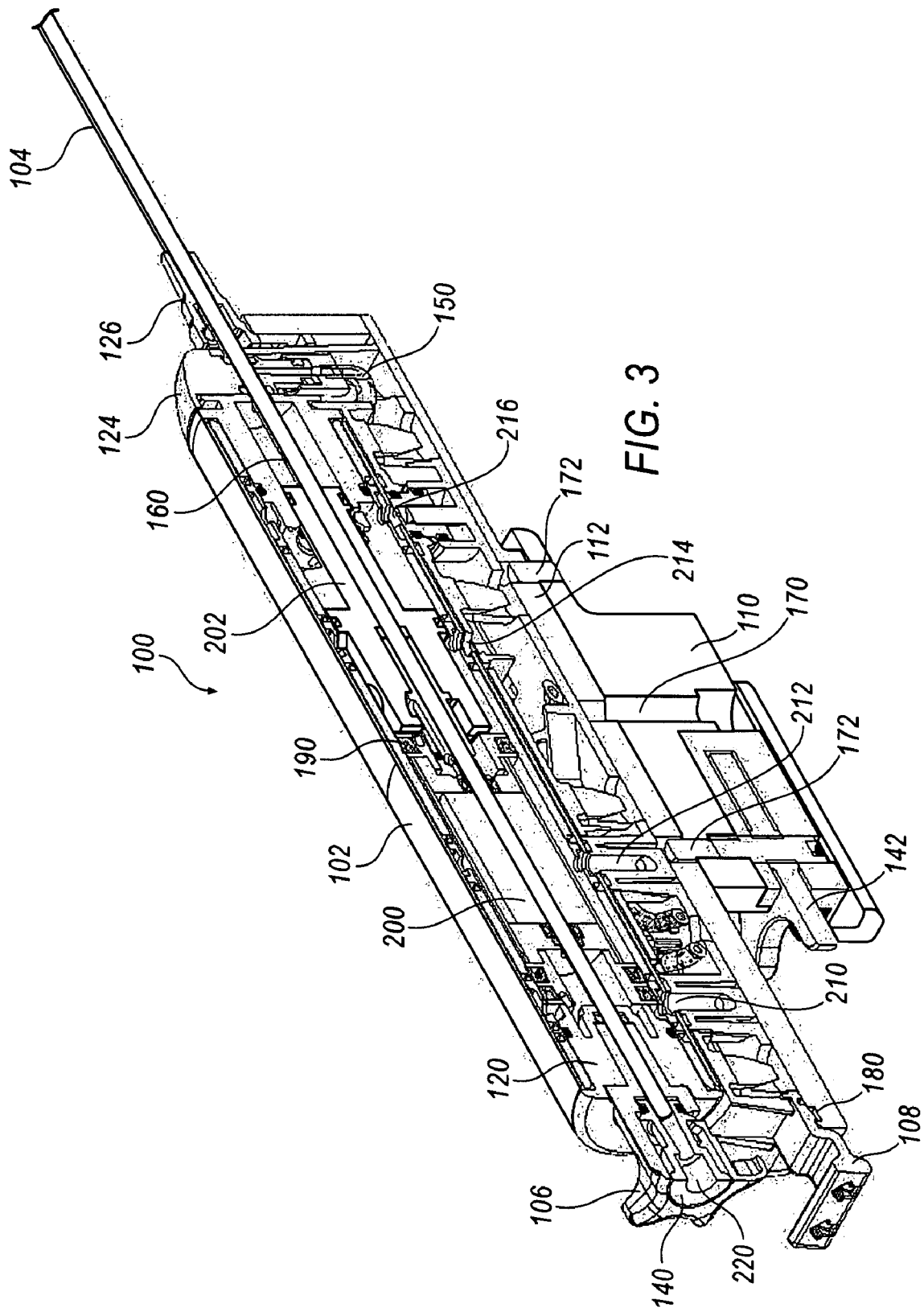
FIG. 3 is a perspective cross-sectional view of the surgical device shown in FIG. 1.

FIG. 3 is a perspective cross-sectional view of surgical device 100 shown in FIG. 1. A holding screw 170 connects bracket 110 to adapter 112. Attachment wheel 142 is turned by the user to tighten bracket 110 onto a positioning system or a stereotactic table. However, bracket 110 is an optional component of surgical device 100. Thus, adapter 112 may be mounted directly to a positioning system or stereotactic table, and thus capable of receiving surgical device 100. When using bracket 110, locating pins 172 are mounted to bracket 110 and are used to locate adapter 112 with respect to bracket 110 along with holding screw 170. Adapter 112 is positively located on locating pin 172. When holding screw 170 is tightly engaged with adapter 112, the two parts are fixedly attached. Thus, when bracket 110 is moved (typically being attached to a movable table), then adapter 112 and surgical device 100 are also moved in unison.

Surgical device 100 itself may be disengaged from adapter 112 by pulling up on latch lever 108, which in turn disengages a latch 180 (described in detail below with respect to FIG. 7C). In the normal course of use, adapter 112 is not removed from the positioning system or stereotactic table and multiple surgical devices 100 may be attached, used, and replaced with new surgical devices 100 for other patients.

Housed within outer sleeve 102 is an inner body 190 that contains moving elements of surgical device 100. Within inner body 190, surgical device 100 further includes an air motor 200 that is fixedly connected to inner cannula 162 (see FIG. 2, not labeled in FIG. 3). In overview, air motor 200 traverses within inner body 190 and acts as a piston to move inner cannula 162 along its axis (explained below in detail with respect to FIGS. 14 and 15). Moreover, air motor 200 also rotates inner cannula 162 to provide improved tissue cutting action. Both a traversal and a rotation of inner cannula 162 are performed using fluid pressure (e.g., air pressure) and are explained below in detail with respect to FIGS. 14 and 15.

A spool 202 is connected to outer cannula 160. The spool fires or retracts outer cannula 160 as explained below in detail with respect to FIG. 4. Spool 202 traverses distally within inner body 190 by way of spring force, which in turn traverses outer cannula 160 distally within introducer cannula 104 (explained below in detail with respect to FIGS. 14 and 15). Spool 202 is traversed proximally using air pressure.

The fluid pressure is selectively presented at locations along outer sleeve 102 at a biopsy port 210, a motor inlet port 212, and a firing port 216. The operation of each port 210, 212, 216 is described in detail below with respect to FIGS. 7-7C. In general, firing line 152 is connected to firing port 216, motor line 150 is connected to motor inlet port 212, and biopsy line 156 is connected to biopsy port 210.

Fitting 140 includes a glue well 220 or barb that is used to connect to tubing that leads to a remote tissue collection canister (see FIG. 11B) or other tissue collection systems. When a vacuum is applied to inner cannula 162, resected tissue is drawn through the length of inner cannula 162 from the sampling aperture 250 to tubing and the remote tissue collection canister mentioned above. An example of a suitable collection canister and filter media is described in co-pending U.S. patent application Ser. No. 11/132,034, entitled "SELECTIVELY OPENABLE TISSUE FILTER," filed Dec. 16, 2005 by Joseph L. Mark et al., the contents of which are included in their entirety herein.

Figure 4:
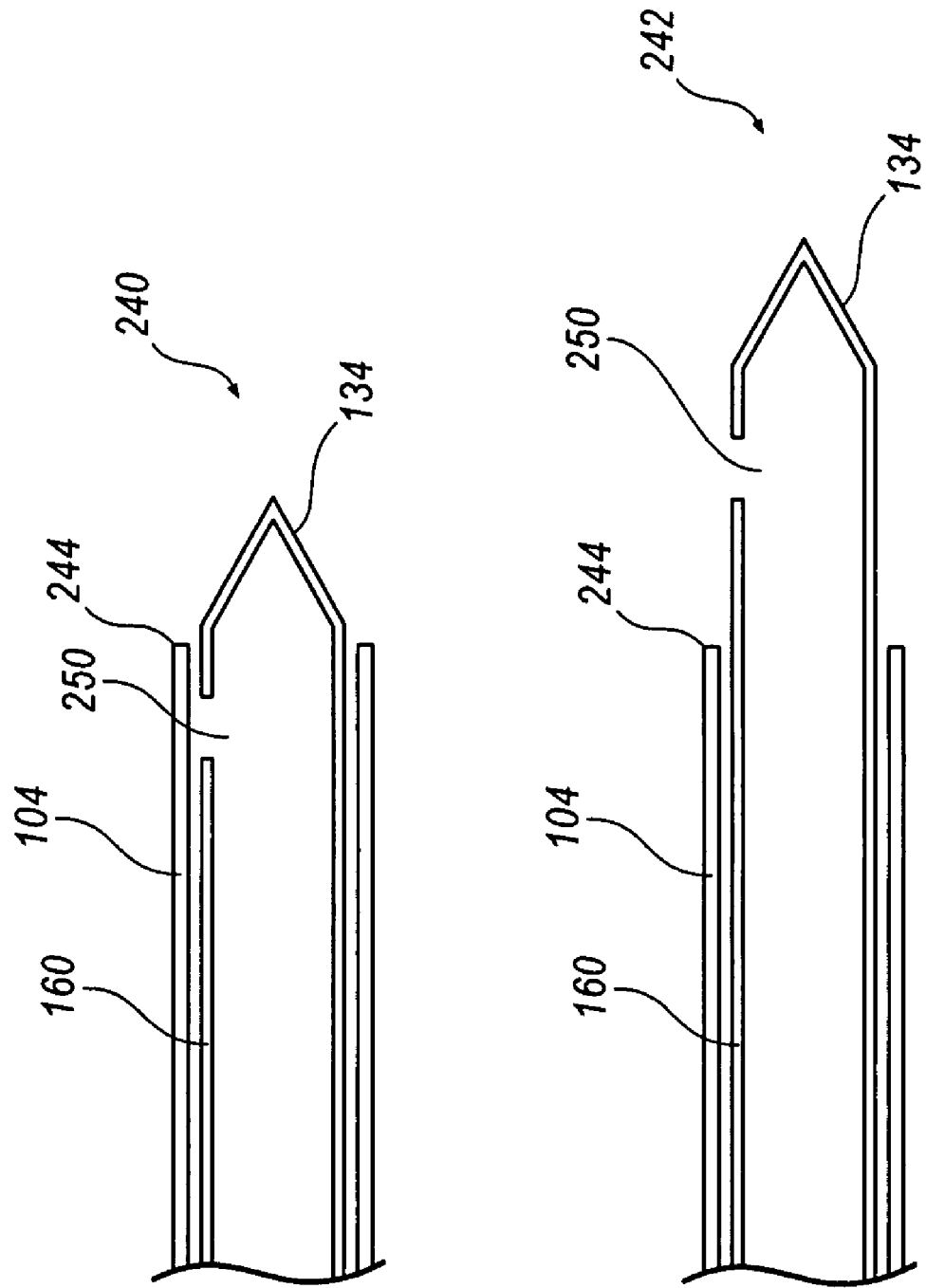
FIG. 4 is a cross-sectional view of an outer cannula of the surgical device of FIG. 1 in a cocked position (top) and a fired position (bottom).

FIG. 4 shows cross-sectional views of outer cannula 160 in a cocked position 240 (top view) and a fired position 242 (bottom view). Introducer cannula 104 with outer cannula 160 inserted in cocked position 240 is used for initial positioning near a target site. When the target site is located, typically using an imaging modality as discussed above, outer cannula 160 is rapidly thrust distally to fired position 242. By quickly thrusting outer cannula 160 to the target site, the tissue is cleanly cut by trocar tip 134 and the target tissue is not moved, pushed, or substantially damaged. When outer cannula 160 is in fired position 242, a sampling aperture 250 is also positioned at the target site. As mentioned with respect to FIG. 1, turning rotator 106 will also turn sampling aperture 250, which is part of cutting element 132. In this way, a surgeon may sample from any angular direction and resect tissue at multiple locations. Inner cannula 162 is not shown for clarity, but is described in detail with respect to FIGS. 6A and 6B.

Figure 5:
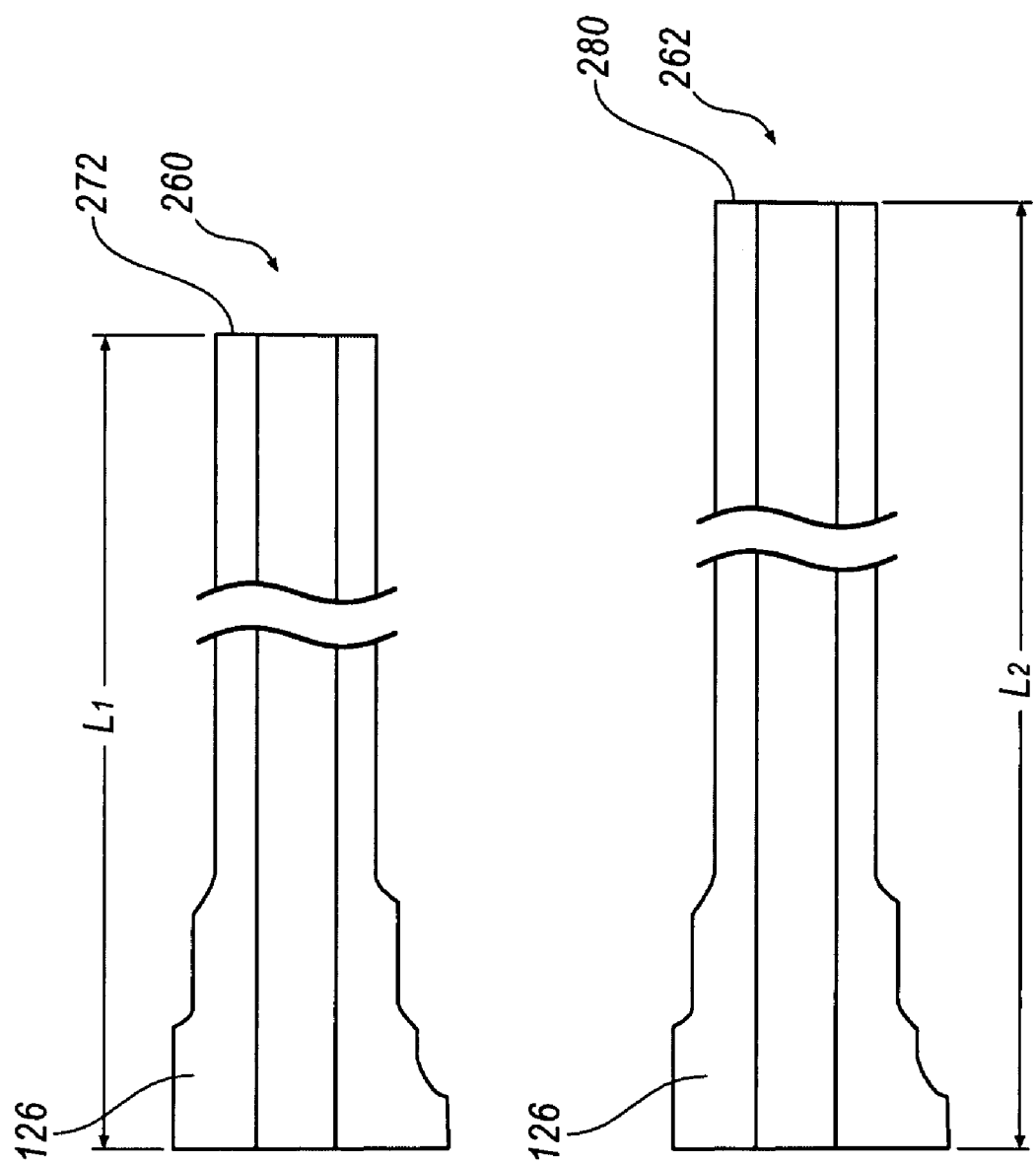
FIG. 5 shows side views of different length introducer cannulas.

FIG. 5 shows side views of different lengths of introducer cannula 104 (shown in FIG. 1), including a first introducer cannula 260 and a second introducer cannula 262. First introducer cannula 260 has a predetermined length of L1. Second introducer cannula 262 is longer overall and has a predetermined length of L2. When introducer cannulas 260 or 262 are attached to surgical device 100, distal ends 272, 280 extend away from surgical device 100 to different distances based on their respective lengths, L1 and L2. By providing different length introducer cannulae, different aperture lengths may be created.

FIG. 6A shows cross-sectional views of tissue prolapsed through sampling aperture 250 using different length introducer cannulas 260 and 262. In an embodiment 268 using first introducer cannula 260, having a length L1, distal end 272 protrudes minimally over sampling aperture 250. When a vacuum is pulled at inner cannula 162, a first amount of tissue 274 prolapses through sampling aperture 250 and is not substantially blocked by introducer cannula 260.

In a second embodiment 270, second introducer cannula 262 is used that has a length L2 which is longer than length L1. Because the distance along outer cannula 160 is fixed, second introducer cannula 262 protrudes at distal end 280 partially over sampling aperture 250 and effectively reduces the size of sampling aperture 250 resulting in a reduced volume of prolapsed tissue 282 entering outer cannula 160. Thus, by using different length introducer cannulas 260, 262 a surgeon is able to determine the effective sampling aperture of surgical device 100 by selectively limiting access to sampling aperture 250. It is contemplated that a length of introducer cannula 104 will leave sampling aperture 250 entirely open, or the length may be configured to substantially close sampling aperture 250, or any length therebetween may control the effective size of sampling aperture 250.

It is understood, that prior to taking a sample of tissue 274/282, inner cannula 162 may be positioned so as to be disposed substantially flush to sampling aperture 250. However, in some situations (depending on a variety of factors), when inner cannula 162 is in this position, vacuum from inner cannula 162 may pull tissue into sampling aperture 250 prior to the cutting stroke. And, if this occurs, the drawn tissue may seal gap 164 between inner and outer cannulae 162 and 160, respectively, thereby creating a vacuum lock on any tissue in the cannula or similar diameter tubing. Thus, if this occurs, the excised tissue may be prevented from freely passing though the inner cannula 162.

FIG. 6B shows cross-sectional views of resected tissue using different length introducer cannulas 260 and 262. In both first embodiment 268 and second embodiment 270, inner cannula 162 is traversed distally and rotated to assist in severing the tissue prolapsed through sampling aperture 250. In first embodiment 268, using first introducer cannula 260, a large amount of resected tissue 284 is present within inner cannula 162. In second embodiment 270, a smaller amount of resected tissue 286 is present within inner cannula 162. The difference in volume of tissue resected is related to the increased or decreased effective size of sampling aperture 250 and the resultant size of prolapsed tissue. Thus, different length introducer cannulas 260, 262 may be used to control the size of tissue resected, and the length of the device to be inserted into the patient. (For example, 270 is a "petite" aperture that may be used on thin breasted women).

Figure 7:
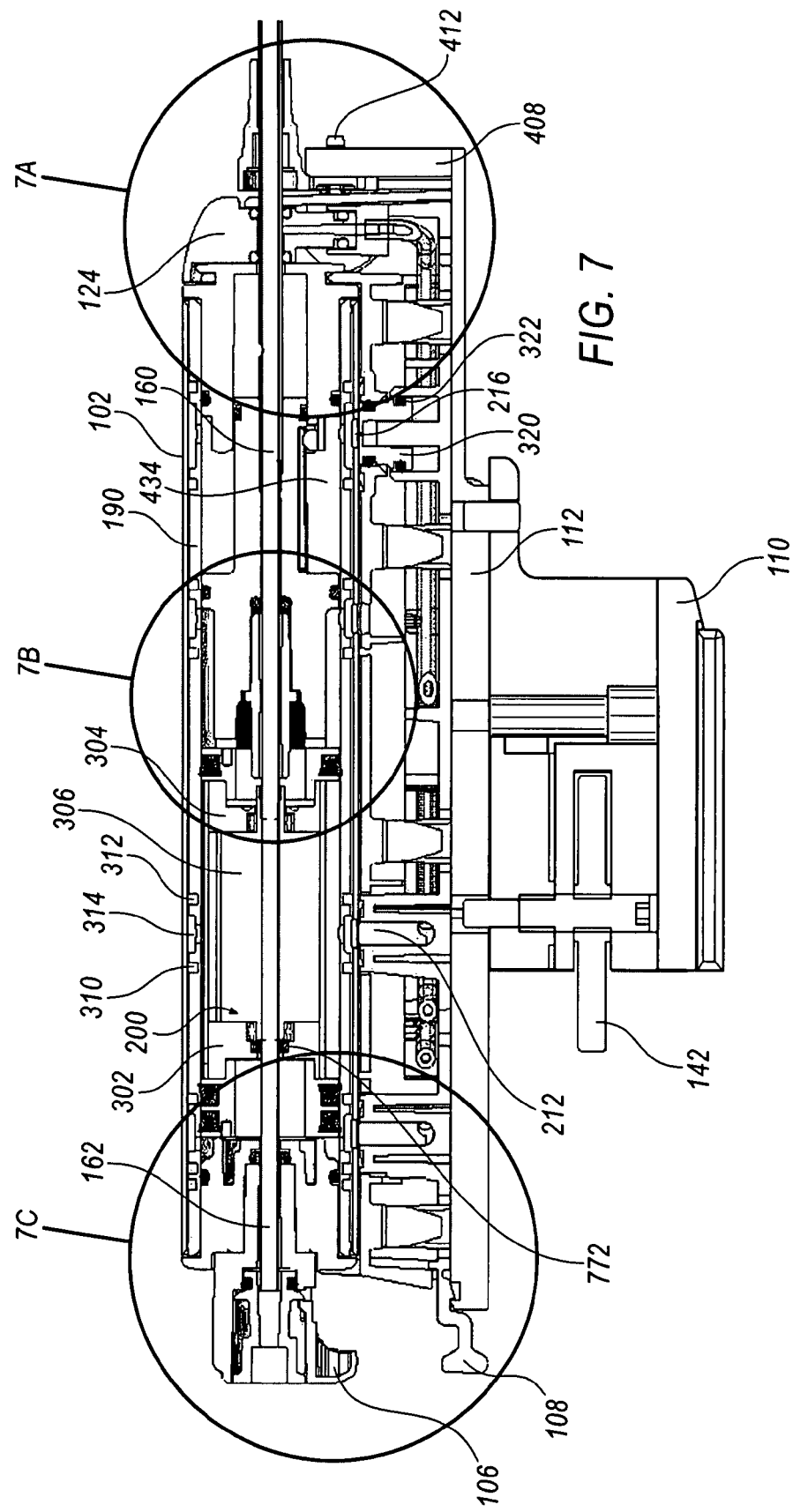
FIG. 7 is a cross-sectional view of surgical device of FIG. 1.

FIG. 7 is a cross-sectional view of surgical device 100 of FIG. 1. For greater detail of the inner components of surgical device 100, refer to FIGS. 7A-7C for the areas of enlargement as shown. By way of example, motor inlet port 212 provides pressure to the interior of inner body 190 by way of a motor inlet pressure groove 314. Motor inlet pressure groove 314, and the pressure applied, is sealed from the rest of inner body 190 using a first annular seal 310 and a second annular seal 312 that are surrounded by outer sleeve 102. Seals 310, 312 are typically o-rings and are configured as floating o-rings. Such groove and ring seal designs are also applied to biopsy port 210, motor exhaust 214, and firing port 216, as explained below in detail with respect to FIG. 7D.

FIG. 7A is a partial enlarged cross-sectional view of the front of surgical device 100 taken from encircled area 7A of FIG. 7. Adapter 112 further includes a wall portion 408 for holding surgical device 100 in place along a front face of surgical device 100. Wall portion 408 cooperates with latch lever 108 to retain surgical device 100. Further, wall portion 408 also provides an attachment point for introducer hub 126. Introducer hub 126 includes a seal 410 that outer cannula 160 and inner cannula 162 protrude through. Additionally, introducer hub 126 includes a lower portion 411 having a hub snap feature 412 that engages wall portion 408. As shown in FIG. 7A, hub snap feature 412 extends from lower portion 411 and extends snaps onto wall portion 408. Hub snap feature 412 may be configured to interfere with, snap into, or selectively engage with wall portion 408, such that wall portion 408 holds introducer cannula 104 (which is attached to introducer hub 126) and introducer hub 126 in place.

The positioning of lower portion 411 proximal with wall portion 408 provides registration of introducer hub 126 to adapter 112. Moreover, when surgical device 100 is selectively attached to adapter 112 and when introducer hub 126 is in place, registration and position relative to each of adapter 112, surgical device 100, introducer hub 126, distal end 130, and cutting element 132 is secured. Such registration allows for precise positioning of cutting element 132 relative to adapter 112 and the target area. Typically, adapter 112 is linked to a positioning table allowing for precise positioning of adapter 112 and surgical device 100. Note that introducer hub 126 is independently attachable to wall portion 408 such that introducer hub 126 may be left attached to wall portion 408 when surgical device is disengaged from adapter 112 and removed from adapter 112.

A first seal 420 and a second seal 422 engage outer cannula 160 to prevent leakage of pressure or fluids from surgical device 100. Outer cannula 160 is slidably and rotatably free to move along its axis with respect to first seal 420 and second seal 422, among other seals described below. Saline line 150 engages a connector 424 near the front portion of surgical device 100. Connector 424 engages with a saline channel 426 and is sealed with a saline o-ring 428. Saline channel 426 is further sealed between first seal 420 and second seal 422 and allows for the flow of saline around outer cannula 160.

When outer cannula 160 is in the fired position (shown translated distally in FIG. 6), a saline port 430 is advanced between first seal 420 and second seal 422. Thus, when saline is forced or pulled by vacuum through saline line 154, through connector 424, saline channel 426, saline enters outer cannula 160 at saline port 430. Under pressure, saline travels distally along gap 164 between outer cannula 160 and inner cannula 162 (described above in detail with respect to FIG. 2). Upon reaching aperture 250 (shown above in detail with respect to FIG. 6), the saline exits the aperture 250 and typically, depending upon placement, flows at the target site. As discussed herein, saline line 154 may be used to deliver liquids, including but not limited to saline, drugs, or treatments to the target site. In one embodiment, saline is injected into the saline line 154. In another embodiment, a closed system is used such that saline is pulled via vacuum from the vacuum line to the inner cannula and back to the saline line.

Figure 7B:
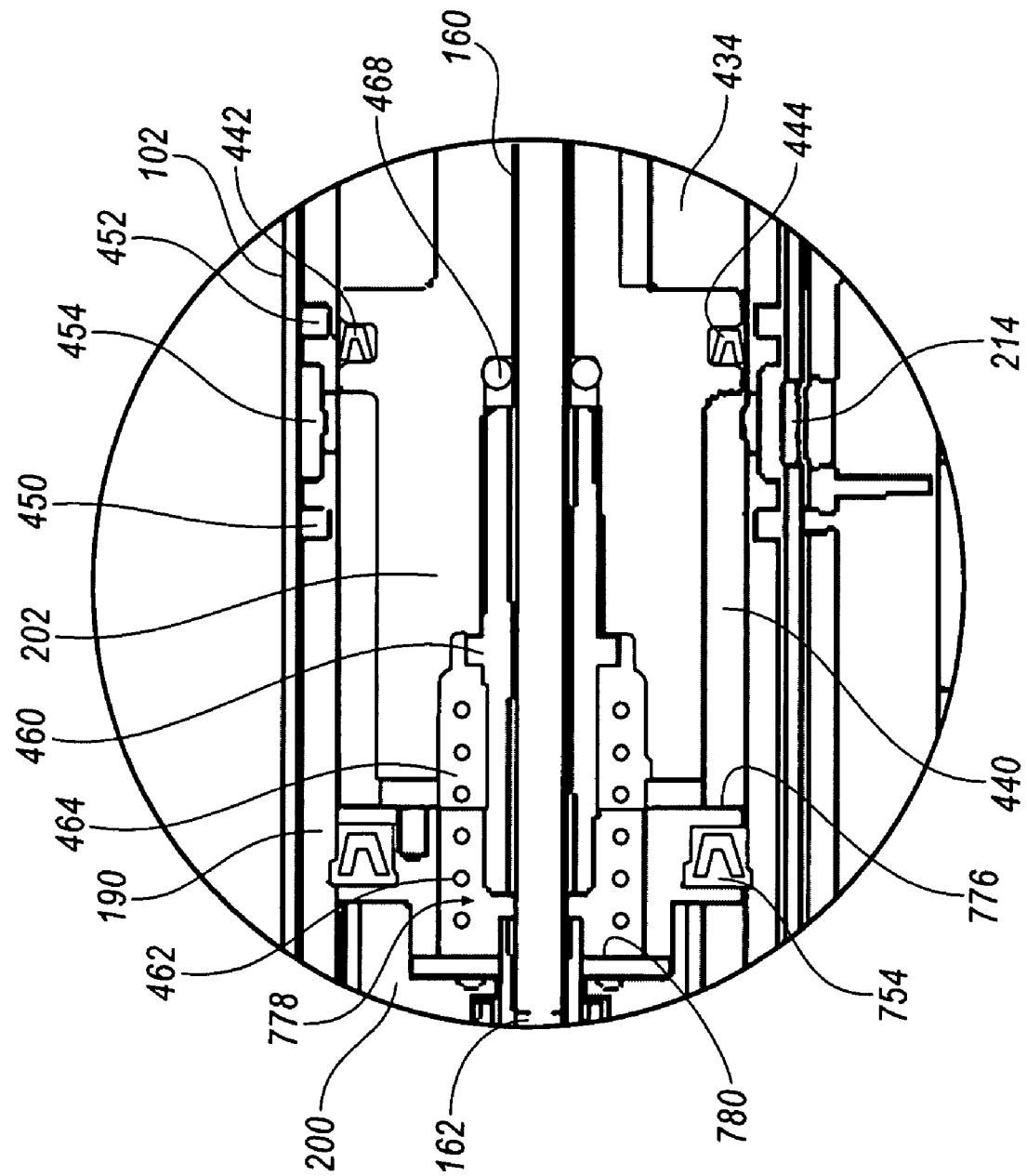
FIG. 7B is a partial enlarged cross-sectional view of a center section of the surgical device taken from encircled area 7B of FIG. 7.

FIG. 7B is a partial enlarged cross-sectional view of a center section of surgical device 100 taken from encircled area 7B of FIG. 7. Outer cannula 160 is fixedly attached to spool 202 by glue (or other suitable adhesives, ultrasonic welding, insert molding, etc.). Thus, when spool 202 moves, so does outer cannula 160. Also attached to spool 202 is a spring guide 460. A spring 462 sits within a spring cavity 464 and spring guide 460 prevents buckling of spring 462 when compressed and preventing interference with inner cannula 162. As shown in FIG. 7B, spring 462 is compressed between spool 202 and air motor 200. The function of spring 462 is described in detail below with respect to FIGS. 14 and 15.

An exhaust chamber 440 is an open space within inner body 190 allowing for movement of air motor 200 distally when spool 202 has moved forward. When air motor 200 is active (by running pressure through the motor portion) air may exit, thereby creating flow, through motor exhaust 214. Additionally, a first seal 450 and a second seal 452 prevent air pressure from motor exhaust from escaping beyond an annular channel 454.

Distally, exhaust chamber 440 is sealed. In one embodiment a cup seal is used. In another embodiment, a ring 442 is seated in an annular groove 444 in spool 202 and by an inner cannula seal 468. A seal 754 on air motor 200 seals exhaust chamber 440 proximally. Inner cannula seal 468 prevents saline flow back into the mechanism and forces the saline toward the distal end of outer cannula 160 (discussed in detail with respect to FIGS. 2 and 7).

Figure 7C:
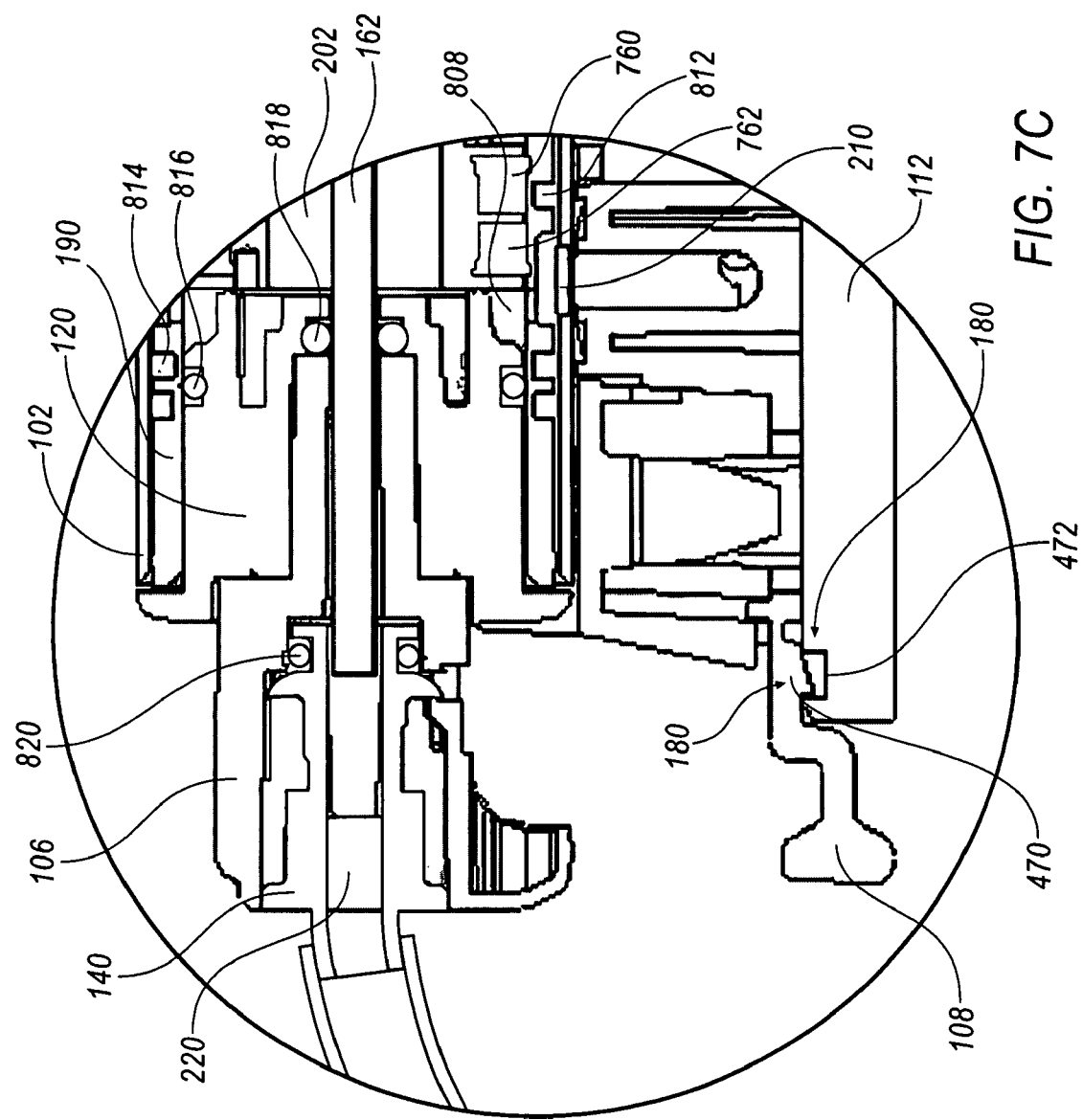
FIG. 7C is a partial enlarged cross-sectional view of the rear of the surgical device taken from encircled area 7C of FIG. 7.

FIG. 7C is a partial enlarged cross-sectional view of the rear of surgical device 100 taken from encircled area 7C of FIG. 7. Latch 180 further comprises a latch tongue 470 that selectively engages a latch slot 472 formed at the proximal end of adapter 112. Pulling up on latch lever 108 disengages latch tongue 470 from latch slot 472 and allows the user to remove surgical device 100 from adapter 112. When the user desires to move air motor 200 distally (described in detail with respect to FIG. 15) air pressure enters at biopsy port 210 and fills biopsy cavity 808. Seals 762 and an inner cannula seal 772 (see FIG. 10A) prevent the pressure from escaping distally and seals 816, 818 at proximal cap 120 prevents pressure from escaping proximally. Thus, when biopsy cavity 808 is pressurized, air motor 200 translates (e.g., moves) distally within surgical device 100.

Inner cannula 162 is sealed at a proximal cap 120 by an o-ring 818. As discussed above, inner cannula 162 is glued (or otherwise fixedly attached) to air motor 200. Thus, when air motor 200 is translated, inner cannula 162 also moves. O-ring 818 allows inner cannula 162 to move while still maintaining a seal between proximal cap 120, biopsy cavity 808, and inner cannula 162. Additionally, fitting 140 is sealed by an o-ring 820. An end of fitting 140 is sealingly received within a distal end of a vacuum line. Thus, when a vacuum is applied to the vacuum line, the vacuum is contained and pulled through sample lumen 166 (see FIG. 2) of inner cannula 162 for removal of tissue and fluids from the target site.

Referring back to FIG. 7, an exhaust piston 320 includes seals 322 and engages firing port 216. Exhaust piston 320 is used to vent a front chamber 434 distal from spool 202 and therefore allows for rapid movement of spool 202 when desired. Exhaust piston 320 further includes a small hole (not shown) at the top of the piston allowing air to pressurize through it. When the pressure in the open cavity distally from spool 202 is greater than the pressure on the bottom of the piston, exhaust piston 320 will move away from firing port 216 and allow for rapid exhaust of gas. This reduced pressure on the bottom of the piston is created by firing a remote valve (see FIGS. 11-13B).

Figure 7D:
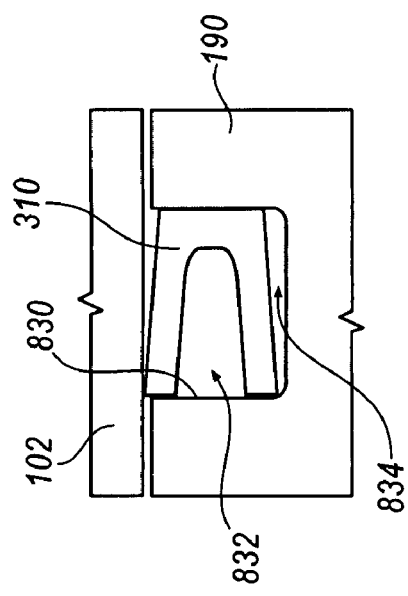
FIG. 7D is a cross-sectional view of a seal shown in FIG. 7.

FIG. 7D is a cross-sectional view of seal 310 (see also FIG. 7). Seal 310 is cup seal that sits in a groove 830 on the outside of inner body 190. In an alternative embodiment, seal 310 may be configured as a floating o-ring. In such an embodiment, a lateral space 832 and a vertical space 834 allow the floating o-ring to move within groove 830.

When pressure is applied, seal 310 moves within groove 830 to seal against inner body 190 and outer sleeve 102. Both seal 310 and the floating o-ring embodiments permit inner body 190 to be turned within outer sleeve 102 without undue friction. Thus, the user may turn cutting element 132 and inner body 190 by light force using rotator 106 (see FIG. 1). In addition to seal 310, seals 312 (see FIG. 7), 450, 452 (shown in FIG. 7B), seal 814 (see FIG. 7C), as well as the other seals between inner body 190 and outer sleeve 102 also may use floating o-rings. Standard O-rings may also be used.

Figure 7F:
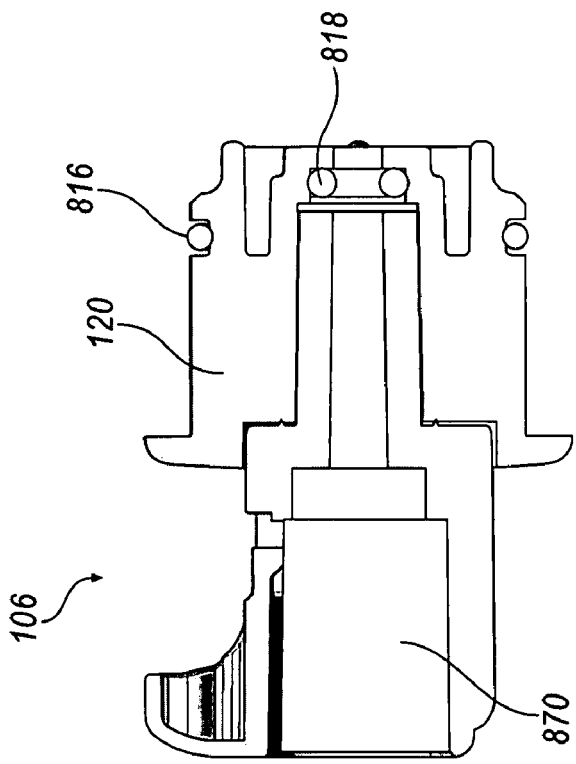
FIG. 7F is a cross-sectional view of the rotator of FIG. 7E.
Figure 7E:
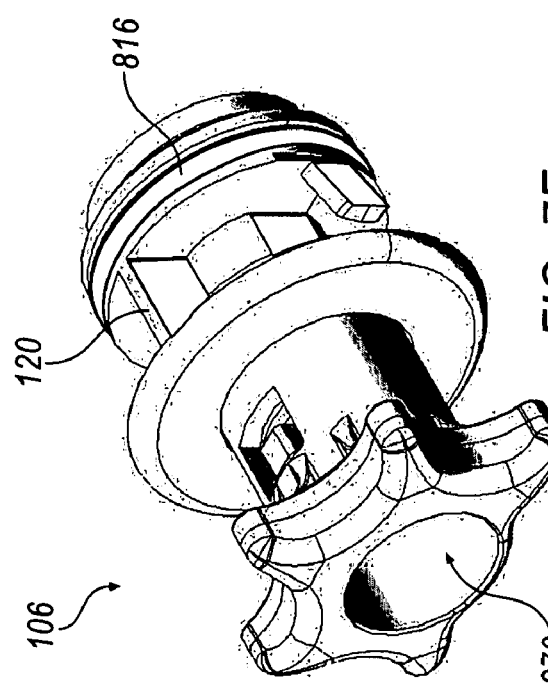
FIG. 7E is a perspective view of a rotator which is used with the surgical device of FIG. 1.

FIG. 7E is a perspective view of rotator 106 which is used with surgical device 100. Proximal cap 120 is used to close off the proximal end of surgical device 100 and seals 816 prevent any pressure from escaping from inner sleeve 102 (see FIGS. 1 and 7C). A receiving portion 870 receives fitting 140 (see FIGS. 1, 3, and 7G) that is pressed/snapped within receiving portion 870 to connect surgical device 100 to a flexible suction line and ultimately a tissue collection system.

FIG. 7F is a cross-sectional view of rotator 106. Seal 818 prevents leakage of pressure around the outer periphery of inner cannula 162 (see FIGS. 2 and 7C). Receiving portion 870 is sized to receive fitting 140 but also allow it to rotate. The rotation allows for the free turning of cutting element 132, without complications caused by twisting of the suction lines.

FIG. 7G is a perspective view of fitting 140 for use with rotator 106 of FIG. 7E. Clue well or barb 220 receives a flexible vacuum line that is used to remove fluids, tissue, etc. from the target site.

FIG. 5A is a cross-sectional view of an embodiment of introducer hub 126 that includes an outer body 700, an inner body 726, and a sealing member 710. Outer body 700 and inner body 726 are typically constructed of a generally rigid plastic material. Sealing member 710 is a flexible sheet material suitable for sealing when perforated by trocar tip 134 (see FIG. 1). Outer body 700 includes an inner interference portion 702 that is held between an outer interference portion 722 and a needle guide 720 of inner body 726. Sealing member 710 is then placed between needle guide 720 and inner interference portion 702. Glue, ultrasonic welding, snap fitting, or other suitable attachment mechanisms are used to prevent separation of outer body 700 and inner body 726.

FIG. 8B is a cross-sectional view of an introducer system 640. Used as a single assembly with surgical device 100, introducer system 640 allows provides for entry, positioning, and placement of medical devices, treatments, and/or markers within a patient. A joining region 650 sealingly connects introducer hub 126 to introducer cannula 104 to form a single generally rigid unit. In operation, trocar tip 134 protrudes just beyond distal end 130 of introducer cannula 104 for insertion within the patient's body (see FIG. 4). When fired, cutting element 132 extends beyond distal end 130 for tissue resection, lavage, delivery of saline or treatments, etc. (see FIG. 4). Moreover, when cutting element 132 is removed from introducer system 640, introducer cannula 104 remains within the patient with distal end 130 precisely positioned at the target area. When surgical system 100 is removed from introducer cannula 104, introducer system 640 may be used as a general purpose access port to the target area. Moreover, sealing member 710 functions as a valve to reduce or prevent leakage of fluids from the patient through introducer cannula 104. A clip-on feature 652 allows for removable placement of introducer system 640 onto a positioning table.

FIG. 8C is an enlarged partial cross-sectional view of introducer system 640, introducer cannula 104 and introducer hub 126. Clip-on feature 652 includes finger actuators 654 and retaining clips 656. These allow the user to easily position and selectively remove introducer system 640 from adapter 112. The interaction with adapter 112 is described in detail below with respect to FIGS. 9A-9I. After introducer system 640 is positioned on adapter 112, trocar tip 134 is pushed through a proximal opening 660 and easily penetrates sealing member 710 when inserted therethrough. Sealing member 710 then closes against the outer periphery of outer cannula 160. If surgical device 100, including outer cannula 160 are removed, sealing member 710 is biased to a normally closed position to prevent fluids from escaping through sealing member. In one embodiment, sealing member by be pre-slit prior to trocar tip 134 being inserted therethrough.

FIG. 9A is a perspective view of adapter 112 for use with surgical device 100 of FIG. 1. FIG. 9B is a side view of adapter 112. Adapter 112 includes a surface 480 and a rail portion 476. The bottom edges of surgical device 100 engage with rail portions 476. Surgical device 100 then slides along surface 480 when surgical device is engaged with or removed from adapter 112. Latch tongue 470 of surgical device 100 selectively engages latch slot 472 (see FIG. 7C). Pulling up on latch lever 108 disengages latch tongue 470 from latch slot 472 and allows the user to remove surgical device 100 from adapter 112 (see FIG. 7C) locking the proximal end of surgical device 100 to adapter 112. When a user places surgical device 100 onto adapter 112, latch tongue 470 moves upwardly over a ramp 474 and engages latch slot 472 to securingly hold surgical device 100 to adapter 112. Wall portion 408 acts as a stop and prevents surgical device 100 from further distal movement when loaded and latch 180 (including latch tongue 470 and latch slot 472) prevents surgical device 100 from moving proximally until latch 180 is disengaged.

An introducer mounting system 490 includes wall portion 408 that receives introducer system 640 and provides a stable attachment point for clip-on features 652 of introducer hub 126 (described above in detail with respect to FIG. 8C, also shown in FIG. 9H). When introducer system 640 is attached to wall portion 408, retaining clips 656 lock in place around a mounting post 492 and introducer cannula 104 is positioned above wall portion 408 at a stabilizing rest 494. In removing introducer system 640 from introducer mounting system 490, the user presses finger actuators 654 together which in turn unlocks retaining clips 656 from mounting post 492.

Adapter 112 may be attached to a positioning table by bracket 110 (see FIGS. 1 and 3). Holes 482, 484, 486 are positioned along adapter 112 to facilitate removable attachment of adapter 112 to bracket 110. For example, holding screw 170 connects with holes 486 (see FIG. 3) and locating pins 172 connect with holes 484 and 488. A slot 488 may be used to prevent overconstraining the adapter when attaching the adapter to a stereotactic table.

FIG. 9C is a perspective view of a trocar holder 540 for use with surgical device 100. FIG. 9D is a side view of trocar holder 540. Trocar holder 540 may be used to hold a trocar device 575 (See FIG. 9G) to facilitate entry into a patient and create a pathway for surgical device 100. Trocar 575 is particularly useful for embodiments of surgical device 100 that have a cutting element 132 that includes a blunt tip, rather than a trocar tip 134.

Trocar holder 540 includes a pair of receiving grooves 542, 544 allow trocar holder 540 to slide along adapter 112 (see FIGS. 9E and 9F). An engagement member is selectively receivable 545 within groove 488 of adapter. Trocar 575, which is separate from surgical device 100, allows a user to pierce the patent's skin and locate introducer system 640 at the target site before surgical device 100 is mounted to adapter 112. Trocar 575 may be used, for example, for thin-when-compressed breasts where the firing mode of surgical device 100 may pose a risk of passing through the breast entirely when the breast is compressed and in cases where the lesion of interest is positioned near the back plate of the stereotactic table. (see FIG. 9I). In such cases, surgical device 100 includes a blunt tip (rather than trocar tip 134 of FIG. 1). Referring to FIG. 9G, in operation, trocar 575 is loaded onto trocar holder 540. The trocar is pushed through introducer system 640 (which is locked on to the end of adapter 112) locked onto adapter at 488 and is manually moved to pierce through the patient's tissue.

The external trocar locks into a pair of seats 550, 552, and spring clip 570 (see FIG. 9C) and is held in place axially (see FIG. 9G). A holder body 560 separates grooves 542, 544 (located at the bottom of trocar holder 540) and seats 550, 552 such that the external trocar is held at the correct height to interface with introducer cannula 104. A directional indicator 562 may be provided to show the user which direction holder body 560 is to be placed on adapter 112 (e.g., the arrow points in the direction of the patient).

FIG. 9E is a perspective view of trocar holder 540 in use with adapter 112. FIG. 9F is a side view of trocar holder 540 in use with adapter 112 and FIG. 9G is a side view of trocar holder 540 with trocar 575 inserted therein. A clip 570 sits within key 554 to hold the external trocar securingly in place.

Thus, a user may insert the trocar by pushing down upon clip 570 with the trocar and it will snap into place into a groove 573 formed on trocar 575. In one embodiment, trocar holder 540 and trocar 575 are designed such that trocar 575 may only fit into trocar holder 540 in the desired configuration. To remove trocar 575 the user may pull up on the trocar to disengage clip 570. In use, external trocar 575 sits on trocar holder 540 and is aligned with the inner lumen of introducer cannula 104 that sits atop stabilizing rest 494. A pushbutton release 572 allows the user to disengage engagement member 545 of trocar holder 540 from adapter 112 so that surgical device 100 may then be installed upon adapter 112 for use.

Figure 10A:
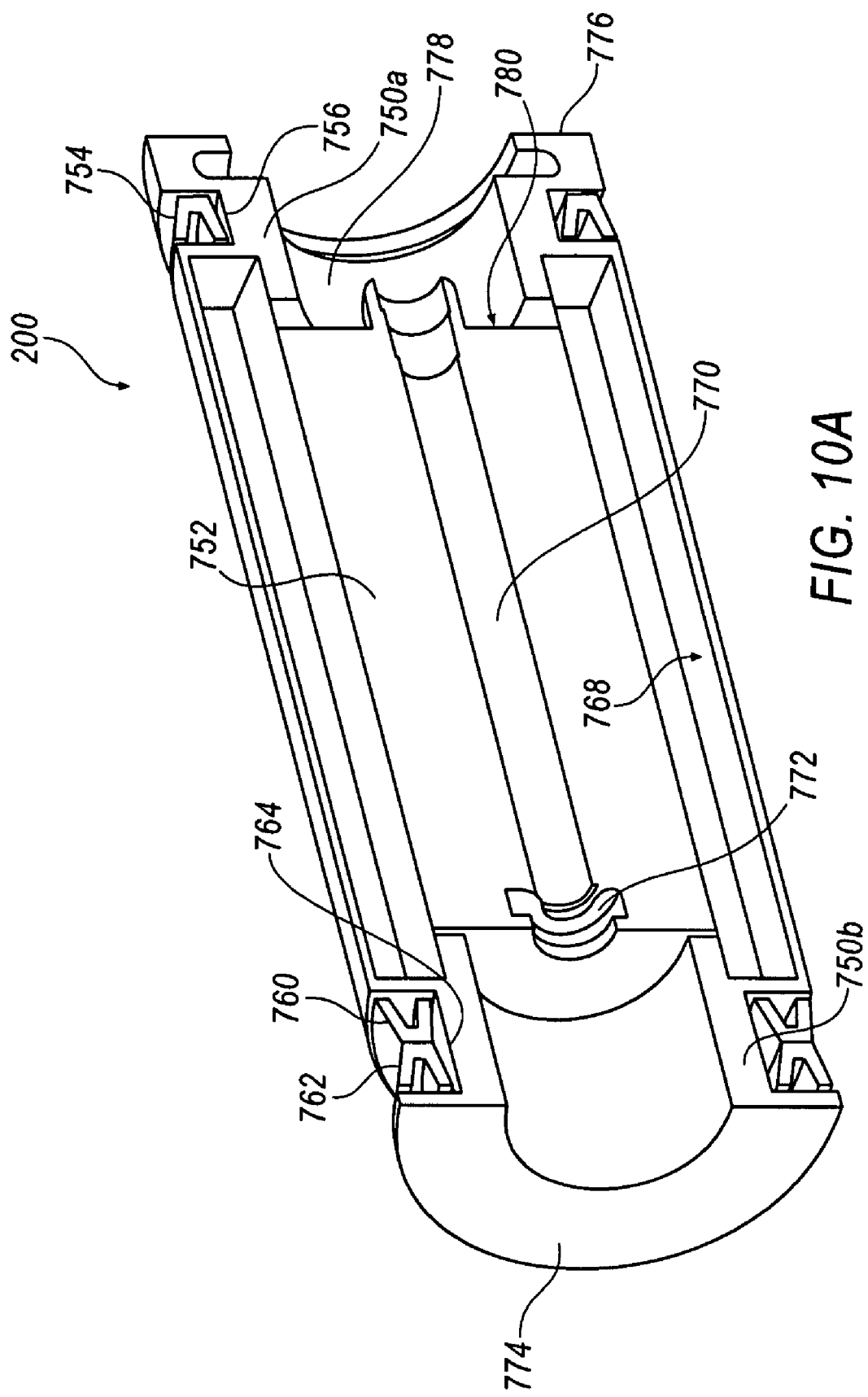
FIG. 10A is a perspective cross-sectional view of an air motor.

FIG. 10A is a perspective cross-sectional view of air motor 200. An example of an air motor 200 and the function thereof is described in detail with respect to co-pending U.S. patent application Ser. No. 11/058,128, entitled "SINGLE MOTOR HANDHELD BIOPSY DEVICE," filed Feb. 15, 2005 by Michael E. Miller, the contents of which are incorporated by reference in its entirety. In general, air motor 200 includes sealing caps 750A, 750B, motor vanes 752, a front seal 754, a first rear seal 760, and a second rear seal 762. Front seal 754 is seated in a front annular channel 756 and is used to seal sealing cap 750A with inner body 190 to create an air motor supply cavity 768 with first rear seal 760. Second rear seal 762 is seated in a rear annular channel 764 and seals sealing cap 750B with inner body 190 to create biopsy cavity 808 (see FIG. 7C). Seals 754, 760, and 762 are embodied as cup seals to improve sealing under certain pressures while still maintaining low friction in motion. However, other known seals, such as o-rings, may also be used.

When first rear seal 760 and front seal 754 are under a pressure applied from operating air motor 200, seals 760 and 754 will expand due to the cup seal configuration. Thus, sealing will be improved when air motor 200 is pressurized. Because biopsy cavity 808 is also selectively pressurized, second rear seal 762 will also expand and provide improved sealing.

Air motor 200 further includes a pass-through 770 for inner cannula 162 to extend through. Inner cannula 162 extends from a distal end (see FIGS. 6A-6B), through air motor 200, to fitting 140. Additionally, inner cannula 162 is fixedly attached to air motor 200 by glue or other suitable material in pass-through 770. Additionally, an inner cannula seal 772 is used to seal air motor 200 with inner cannula 162. Sealing cap 750A further includes a spring guide 778 and sealing cap 750B further includes a rear face 774. Air motor 200 also includes a rotor 780, explained in detail below with respect to FIG. 10B, that provides for rotary motion of inner cannula 162. As shown in FIG. 7C, rear face 774 forms a movable boundary for biopsy cavity 808. Thus, when biopsy cavity 808 is sufficiently pressurized, the force applied to rear face 774 translates air motor 200 distally. Alternatively, when biopsy cavity 808 is vented, spring 462 (see FIG. 7B) translates air motor 200 proximally. Thus, air motor 200 provides a rotary motion to inner cannula 162, as well as translation distally and proximally.

Figure 10B:
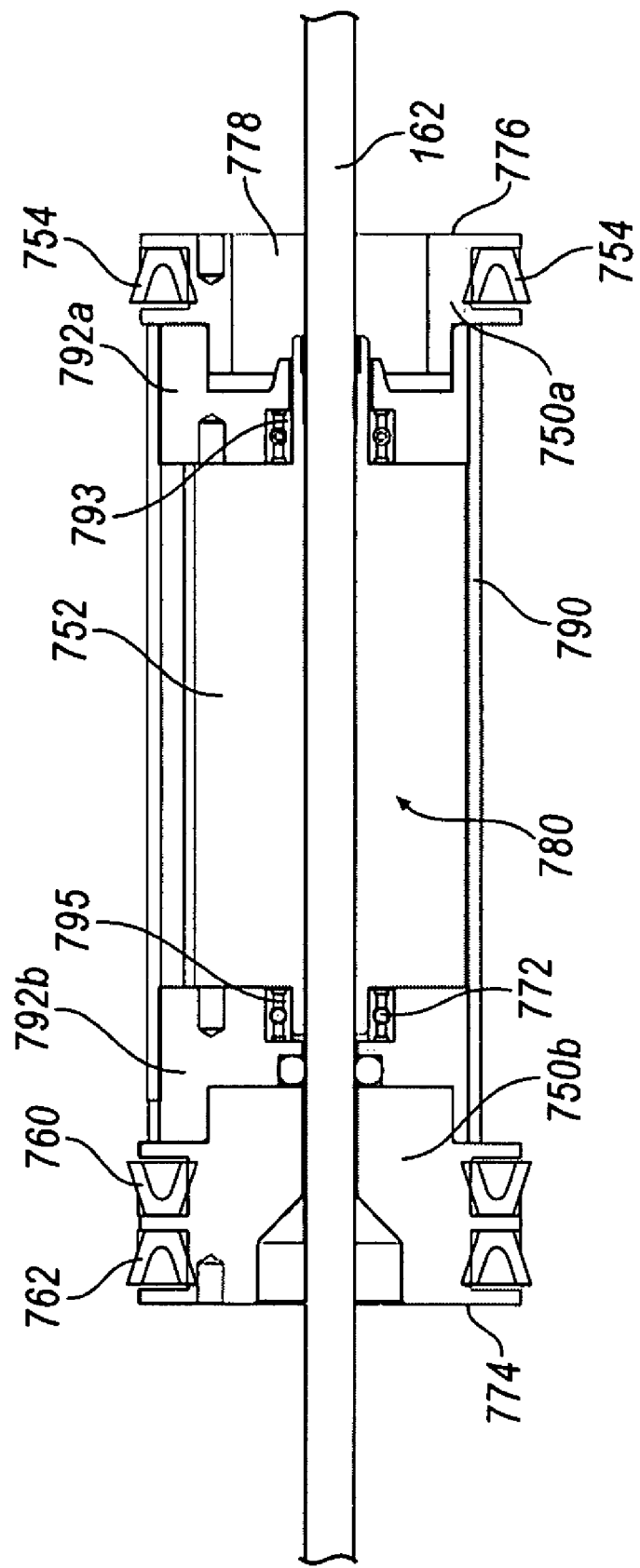
FIG. 10B is a side cross-sectional view of the air motor of FIG. 10A.

FIG. 10B is a side cross-sectional view of the air motor of FIG. 10A. A motor outer housing 790 contains rotor 780 that is configured to spin with the addition of air pressure as a power source. Rotor 780 includes vanes 752. Rotor is attached to inner cannula 162 by glue or by a press-fit. When air pressure is supplied to air motor 200, vanes 752 and rotor rotate about the axis of inner cannula 162 and by virtue of their attachment, also rotate inner cannula 162. A distal bearing 793 and a proximal bearing 795, e.g. ball bearings or roller bearings, allow rotor and vanes 752 to rotate within motor outer housing 790. A distal motor end cap 792A and a proximal motor end cap 792B provide backing for distal bearing 793 and a proximal bearing 795 to ride between. Distal motor end cap 792A and a proximal motor end cap 792B also seal motor outer housing 790 at each end, providing an air-tight cavity for vanes 752 to rotate within.

Figure 11A:
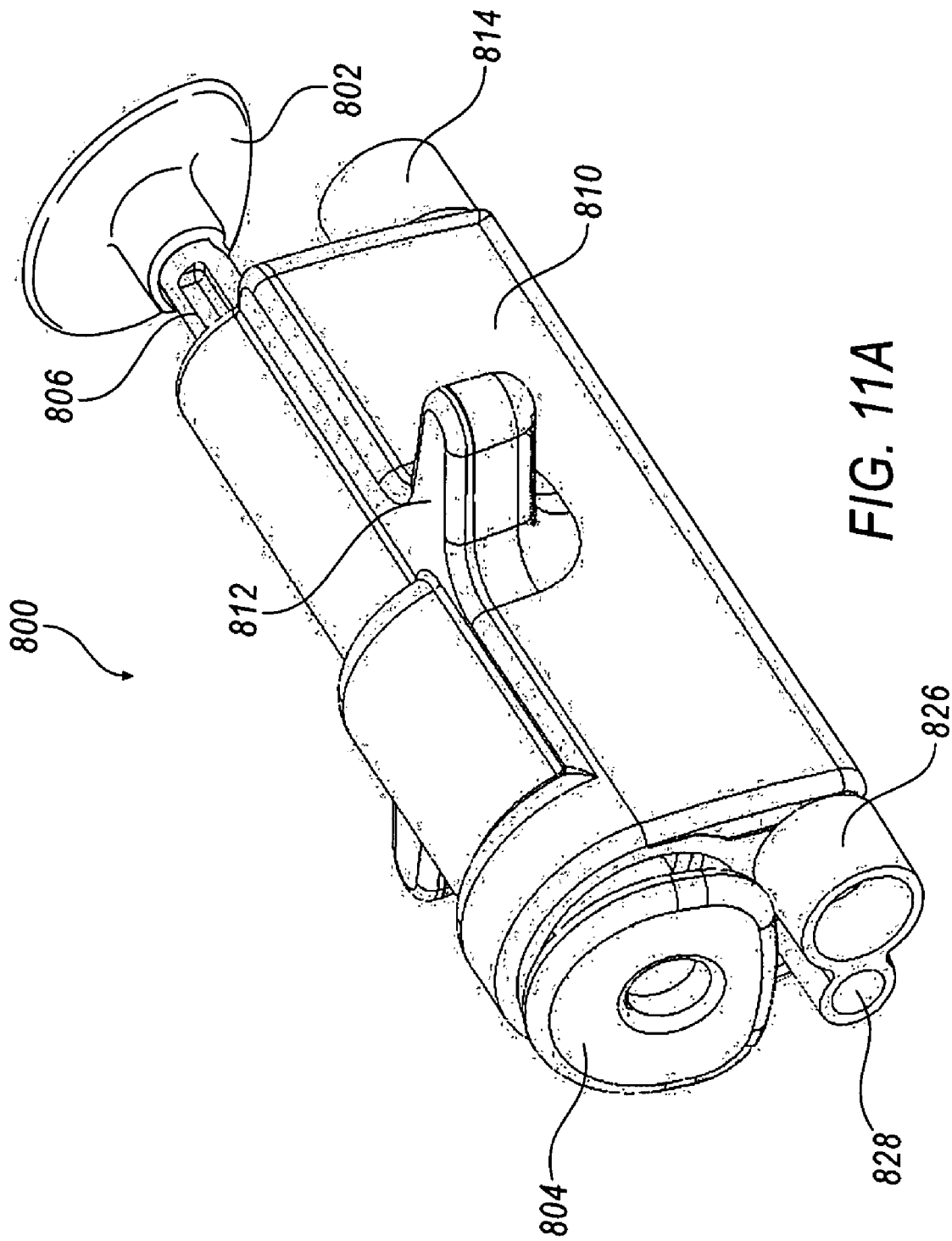
FIG. 11A is a perspective view of a remote valve according to an embodiment.

FIG. 11A is a perspective view of remote valve 800. Remote valve 800 includes a firing button 802, a cocking button 804, an actuator rod 806, a remote valve body 810, and finger bars 812. Air pressure from a console (not shown) enters remote valve 800 at console inlet 814. Firing line 152 (see FIG. 1) is sealingly engaged to firing port 828. Biopsy line 156 (see FIG. 1) is sealingly engaged to biopsy port 826. When firing button 802 is pressed toward remote valve body 810, pressure is vented from firing port 828 and firing line 152 and outer cannula 160 is rapidly extended distally (described in detail with respect to FIGS. 4, 14, and 15). Pressure is then applied to biopsy port 826 and biopsy line 156. When cocking button 804 is pressed towards remote valve body 810, pressure is vented from biopsy port 826 and biopsy line 156 and pressure is then applied to firing port 828 and firing line 152.

Figure 11B:
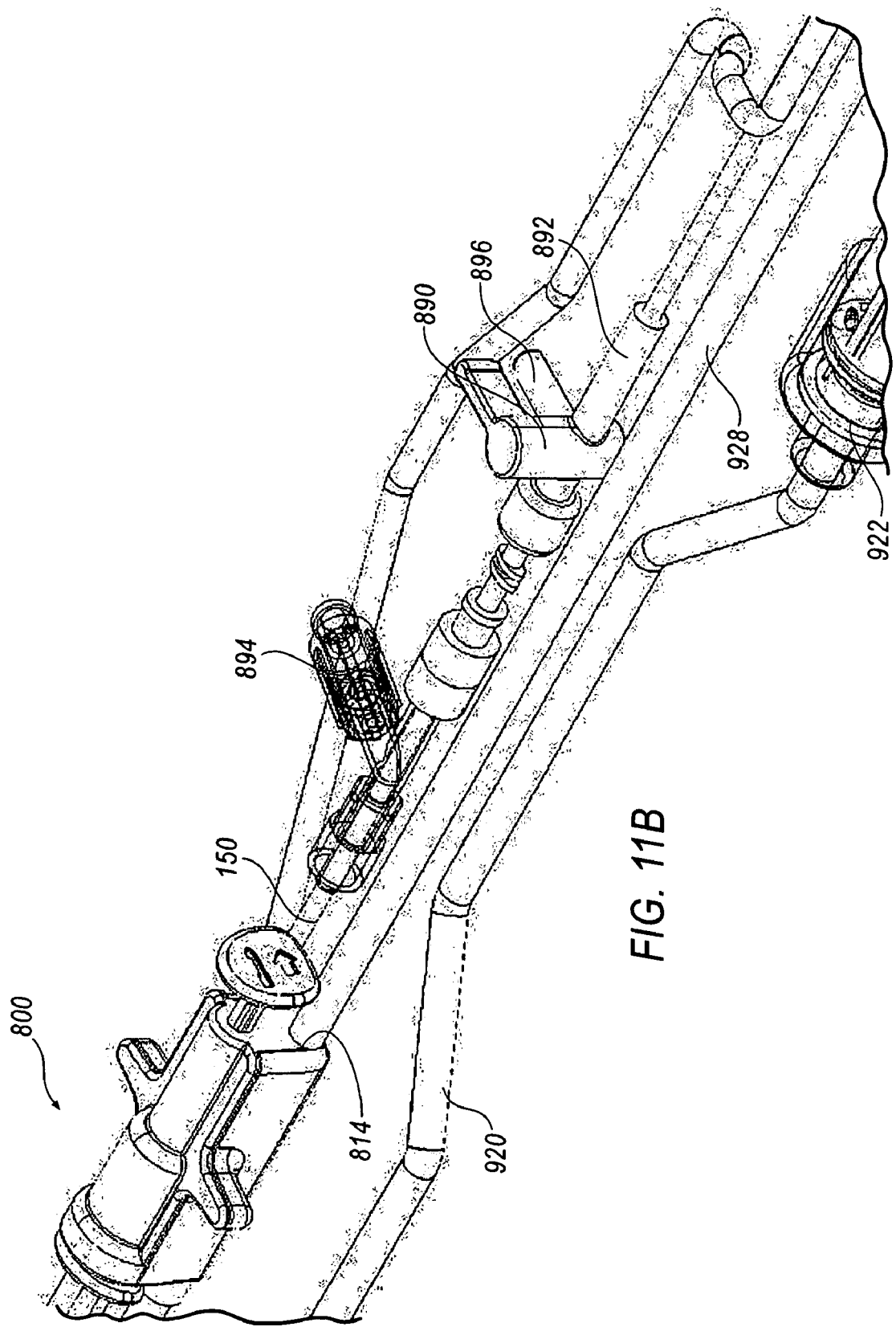
FIG. 11B is a perspective view of the remote valve of FIG. 11A in a tubing arrangement for use with the surgical device of FIG. 1.

FIG. 11B is a perspective view of remote valve 800 in a tubing arrangement for use with surgical device 100. An aspiration line 920 is connected to glue well 220 and ultimately to inner cannula 162 (see FIG. 3). Aspiration line 920 provides vacuum from console 194 and is used to pull fluids, tissue, and/or generally remove irrigation from the target site. A removable tissue filter canister 922 is connected in-line with aspiration line 920 where harvested tissue may be collected for analysis. Console inlet 814 (see also FIG. 11A) is connected to a pressure line 928 which is controlled by console 194.

Saline line 154 is connected to surgical device 100 (see FIG. 1) and to a selectively closable valve that may include a stopcock 890 or a fitting (i.e., a luer lock) that may be selectively opened and closed. A saline port 892 is associated with stopcock 890. Saline port 892 connects to a saline source (e.g., a saline bag) but may also be connected to other types of liquid sources such as bag containing a treatment fluid. Saline line 150 may also include an injection port 894 that allows a user to inject substances to be transported to the target site. In one example, a user may inject an anesthetic into injection port 894 and the anesthetic may be transported to the target site along with saline or alone. Stopcock 890 may also be selectively activated close-off the saline source from saline port 892 allowing saline line 150 to be vented to the atmosphere through an atmospheric line 896. This allows the user to selectively aspirate the target site, aspiration line 920, and collection canister 922, for example, after tissue is resected to remove fluids from the system.

Figure 12A:
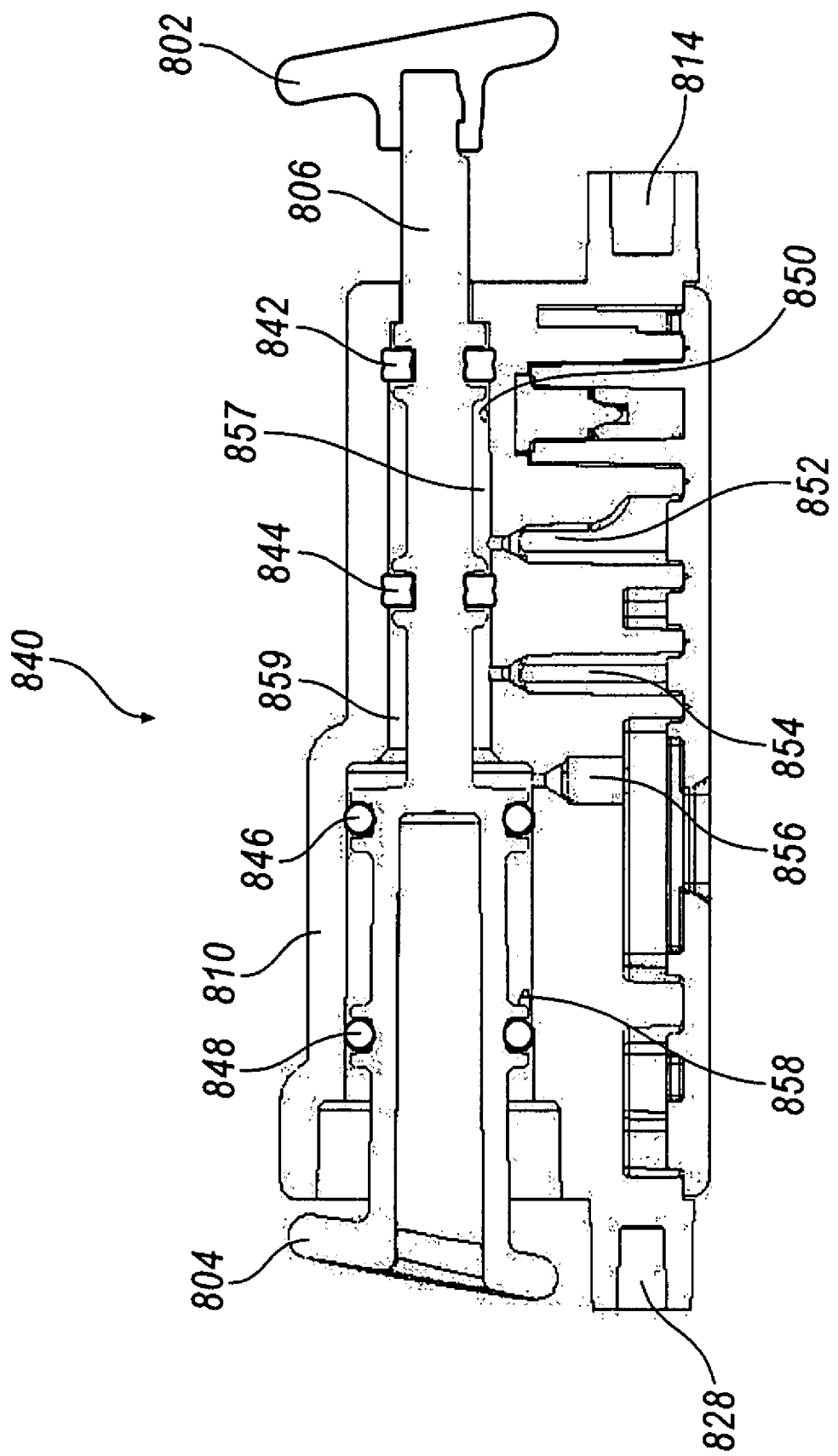
FIG. 12A is a cross-sectional view of remote valve in a cocked position.

FIG. 12A is a cross-sectional view of remote valve 800 in a cocked position 840. Remove valve 800 includes a first port 850, a second port 852, a third port 854, a fourth port 856, and a fifth port 858. First port 850 and fifth port 858 are connected to firing port 828 and firing line 152. First port 858 also includes a one-way check valve that does not allow pressure from firing line 152 to flow into remote valve 800 (also described with respect to FIGS. 13A and 13B). For example, if the console is turned off or inlet air to remote valve 800 is removed, then the check valve will keep the device in the cocked position. Second port 852 is connected to console inlet 814 and a pressure source. Third port 854 is connected to biopsy port 826 and biopsy line 156. Fourth port 856 is open to the atmosphere and serves as a vent.

Actuator rod 806 extends through remote valve 800 and includes a first seal 848, a second seal 846, a third seal 844, and a fourth seal 842. Seals 846 and 848 may be configured as o-rings. Seals 842 and 844 may be configured as quad-rings (or four-lobed rings having parting lines away from the sealing surface) to prevent pressurized air from first port 850, and third port 854 from venting as seals 842, 844 pass over them. As actuator rod 806 is traversed through remote valve body 810, seals 842, 844, 846, 848 create air flow regions for ports 858, 856, 854, 852, 850 to selectively connect to each other or vent to the atmosphere to control operation of surgical device 100. As shown in FIG. 12A, remote valve 800 is in a cocked position 840 where second port 852 is connected to first port 850 by way of seals 842 and 844 that and cavity 857 between actuator rod 806 and remote valve body 810. Cocked position 840 provides that air motor 200 and spool 202 are in their proximal most positions within surgical device 100 (see FIG. 3). If the console were turned off while surgical device 100 was in the cocked position, air would remain in exhaust chamber 440 (see FIG. 7B) and surgical device would remain in the cocked position until remote valve 800 were further manipulated due to the check valve.

Figure 12B:
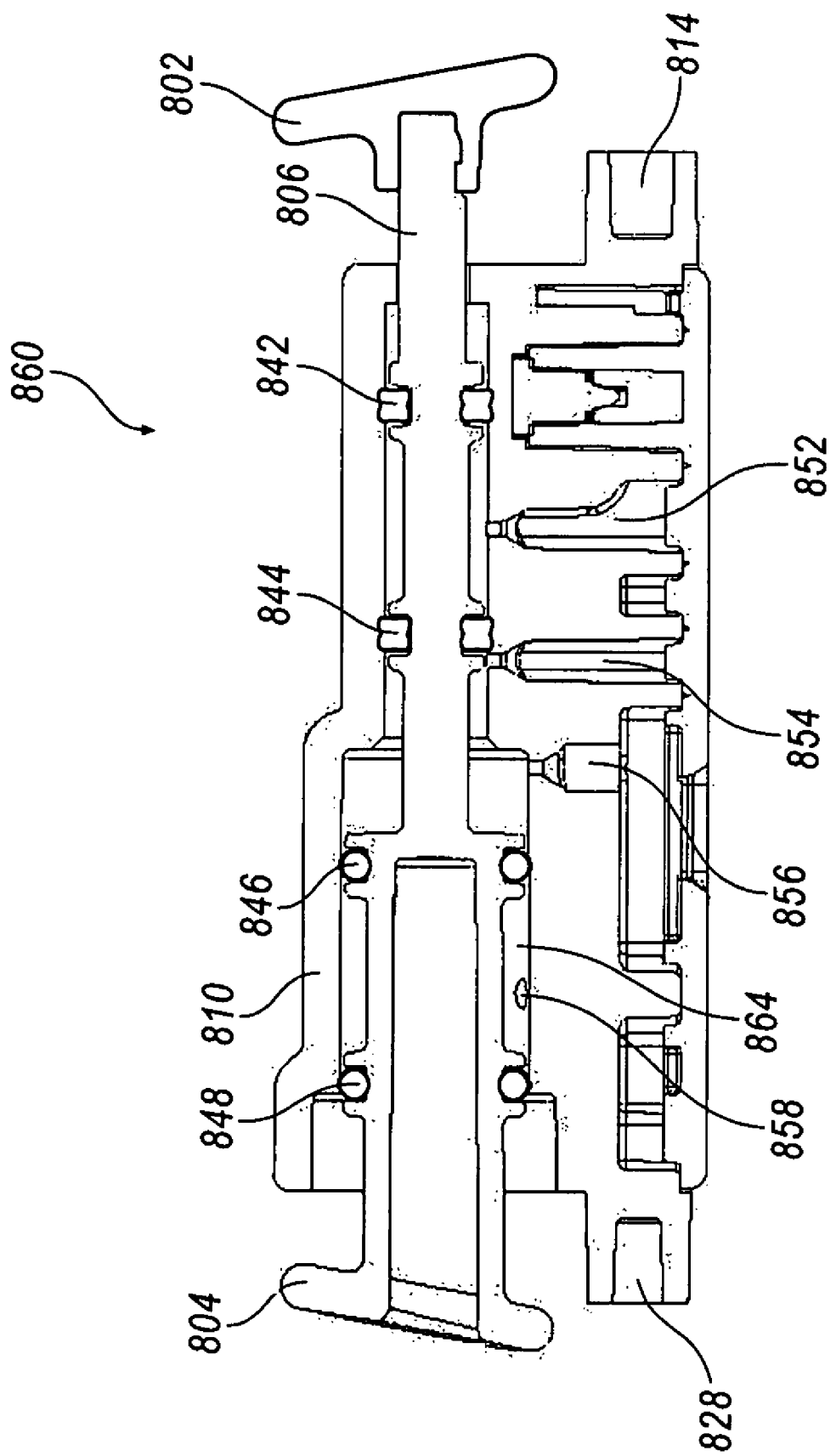
FIG. 12B is a cross-sectional view of remote valve in an intermediate position.
Figure 12C:
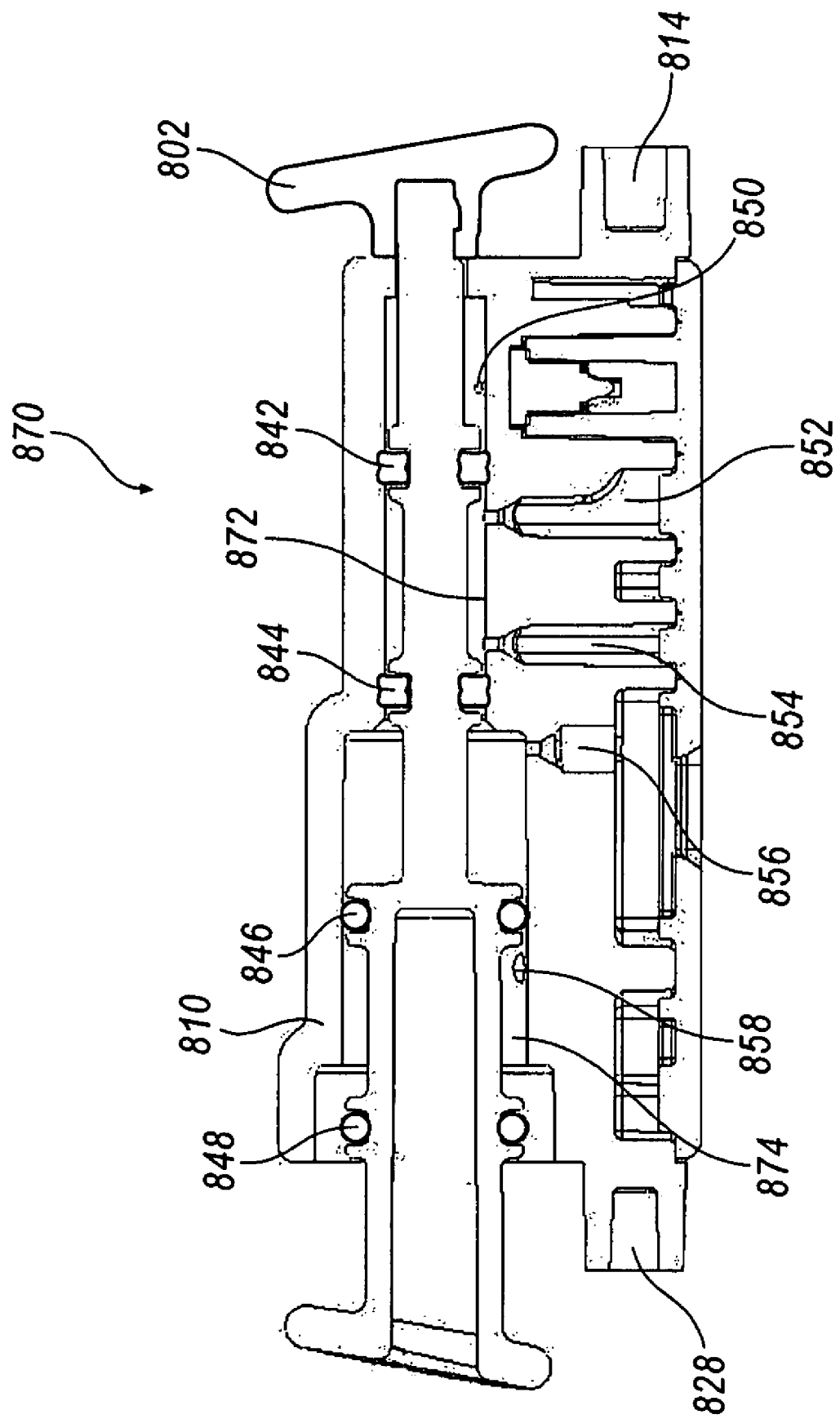
FIG. 12C is a cross-sectional view of remote valve in a fired position.

FIG. 12B is a cross-sectional view of remote valve 800 in an intermediate position 860 between cocked position 840 (see FIG. 12A) and a fired position 870 (see FIG. 12C). Seal 842 is positioned over first port 850. Second port 852 is effectively isolated by first seal 842 and second seal 844. Moreover, first seal 848 is prepared to disengage from the inner periphery of remote valve body 810 and become free to the surrounding atmosphere (see FIG. 12C below).

FIG. 12C is a cross-sectional view of remote valve 800 in fired position 870. First seal 848 is open to the atmosphere resulting in fifth port 858, firing port 828, and firing line 152 being exhausted. For example, port 858 is open to the atmosphere via passage 874 as first seal 848 is no longer contacting remote valve body 810. Fired position 870 contrasts with the embodiment of FIG. 12A where first seal 848 is in sealing contact with remote valve body 810 and second seal 846 and first seal 848 seal port 858 therebetween.

Because first seal 848 is an o-ring and is exhausted directly to the atmosphere across the entire circumference of the O-ring, rather than through a port (see FIGS. 12A and 12B), a larger volume of air may be exhausted. Such a rapid exhaust assists in the rapid deployment, or firing, of spool 202 and outer cannula 160 (see FIGS. 4 and 14).

Third port 854 is then connected to second port 852, console inlet 814, and a pressure source from a console (not shown). When third port 854 and second port 852 are connected by virtue of first seal 842, second seal 844 and cavity 872, pressure is applied to biopsy cavity 808 and air motor 200 is moved forward in biopsy mode slightly after spool 202 is fired forward (described in detail below with respect to FIG. 15).

FIG. 13A is a cross-sectional view of an alternative embodiment of a remote valve 880 in a cocked position. Remote valve 880 includes a thumb trigger 882, a pressure port 888, and a pressure channel 886. Thumb trigger 882 is used to move a valve body 884 within remote valve 880. Valve body 884 further includes a first seal 904, a second seal 902, and a third seal 900. Port 912 and check valve 910 are connected to firing line 152. Vent ports 892 and 894 are open to the atmosphere. Check valve 910 prevents pressure from firing line 152 from entering remote valve 880. However, check valve 910 allows pressure from pressure port 888 (connected to a console) to pressurize firing line 152. When in the cocked position, seals 900 and 902 prevent pressure from pressure port 888 from escaping anywhere other than through check valve 910. Seals 902 and 904 prevent port 912 from venting the pressure of firing line 152.

FIG. 13B is a cross-sectional view of an alternative embodiment of a remote valve 880 in a fired position. Thumb trigger 882 is moved forward and thus, moves valve body 884. Port 912 is open to the atmosphere via vent 892. Thus, firing line 152 is also vented to the atmosphere. Then, pressure port 888 then pressurizes biopsy line 156 and is sealed by seals 900 and 902. The sequence is reversed to go from a fired to a cocked position.

Figure 14:
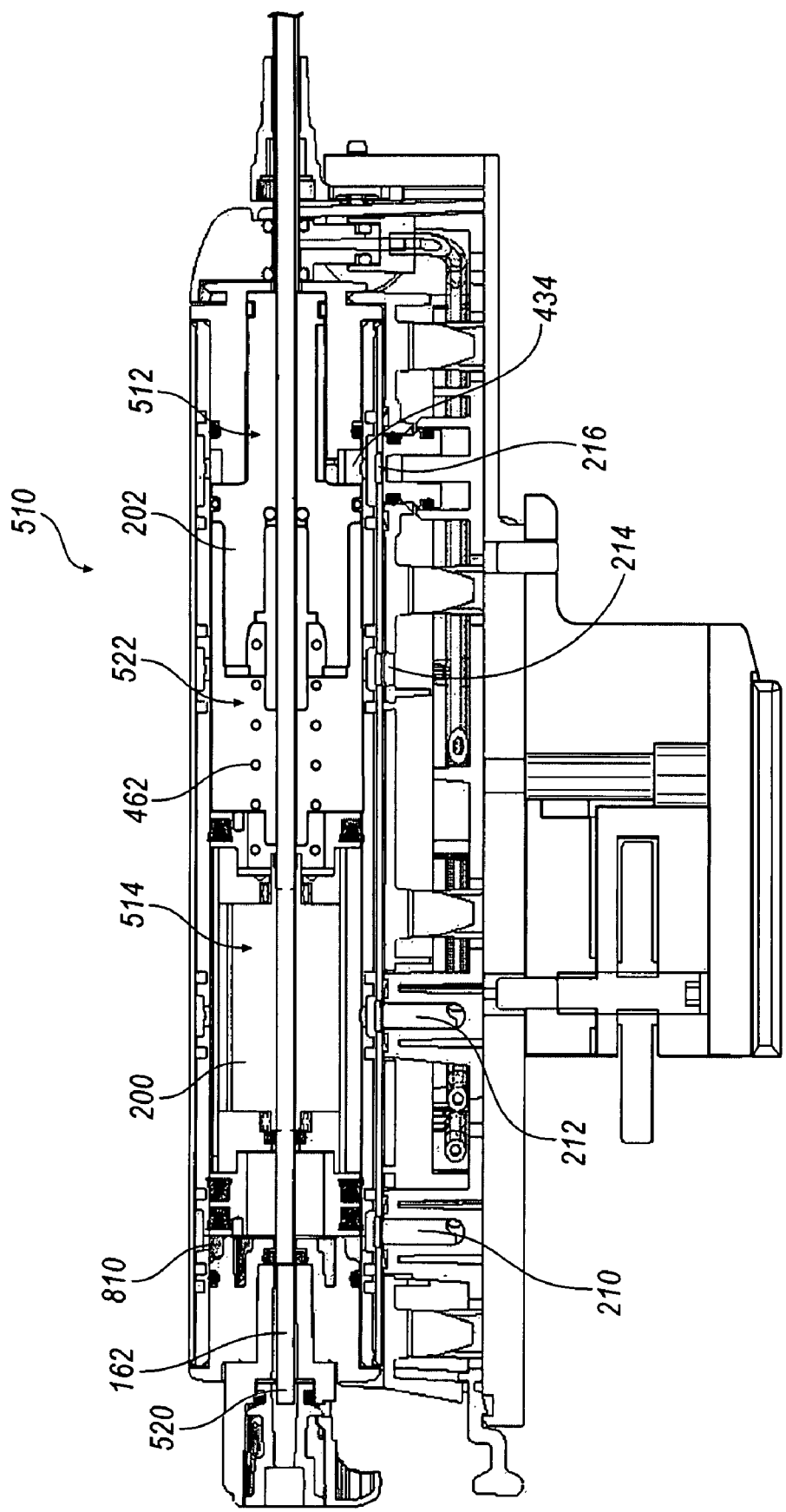
FIG. 14 is a cross-sectional view of the surgical device of FIG. 1 in a fired position with the inner cannula retracted.

FIG. 14 is a cross-sectional view of surgical device 100 in the fired position 510 with inner cannula 162 retracted. Air pressure is removed from firing line 152 which reduces pressure under exhaust piston 320. Exhaust piston 320 then moves downwardly and spool cavity 434 is vented to the atmosphere. A rapid escape of pressure at firing port 216 allows for spring 462 to thrust spool 202 distally and fire outer cannula 160 to the target site (see FIG. 4). Spring 462 is left in an extended position 522 and spool 202 is left in a fired position 512. Air motor 200 is in a proximal position 514 without air pressure applied to biopsy line 156 and biopsy port 210. Thus, inner cannula 162 is also distally positioned. The action of firing surgical device 100 is effected by remote valve 800 (described in detail with respect to FIGS. 11-12C, and shown in the fired position with respect to FIG. 12C).

Figure 15:
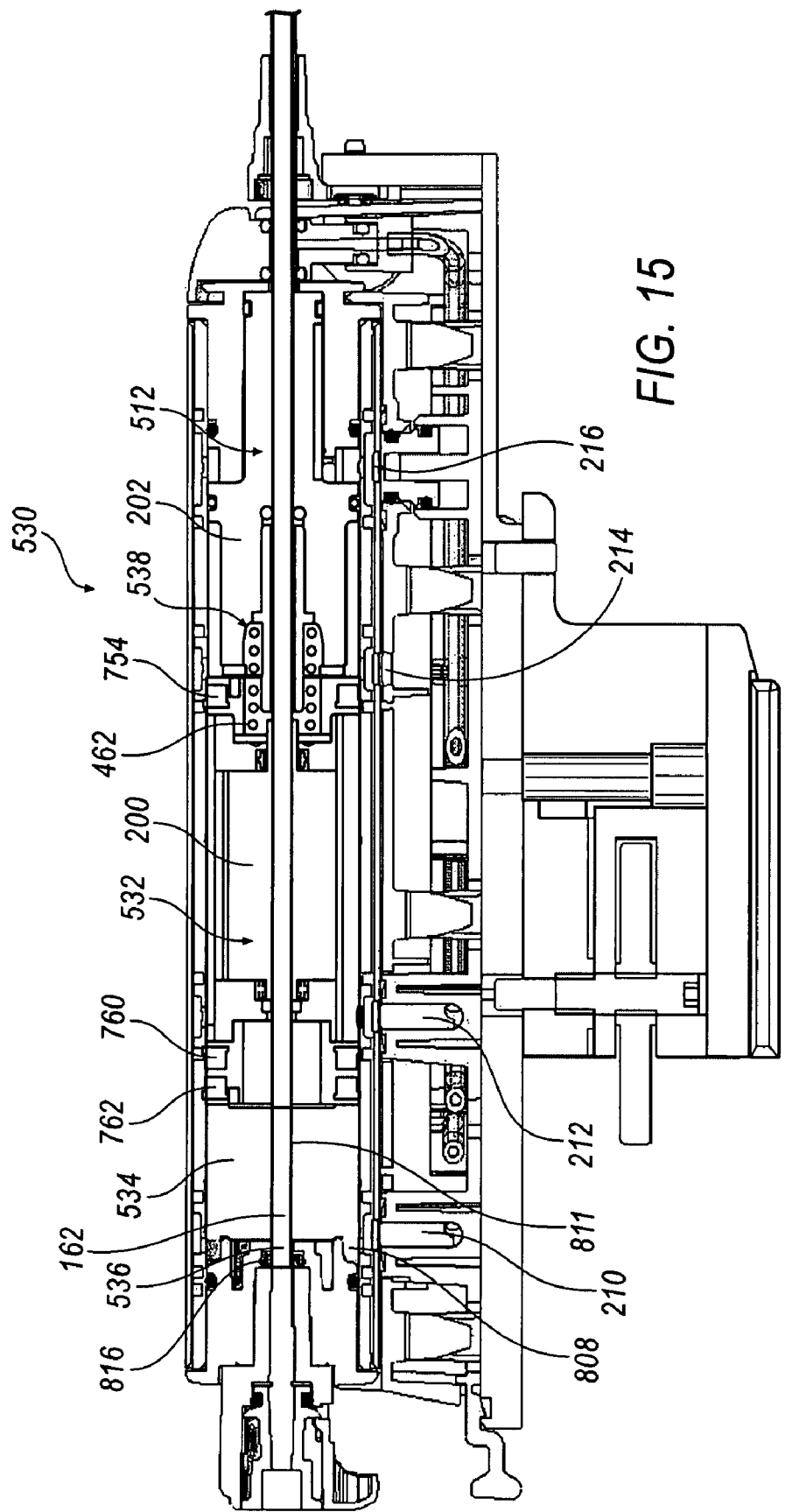
FIG. 15 is a cross-sectional view of the surgical device of FIG. 1 in a fired position with the inner cannula advanced.

FIG. 15 is a cross-sectional view of surgical device 100 in the fired position 530 with inner cannula 162 advanced. Air pressure is applied to biopsy port 210 and biopsy cavity 808 where the pressure moves air motor 200 distally. A larger biopsy cavity 811 is created from the movement of air motor 200 distally. Inner cannula 162 also moves distally by virtue of being fixed to air motor 200. In the distal position, tissue is severed at the target site (see FIG. 6B). The tissue is drawn proximally along inner cannula 162 which remains sealed by o-ring seal 816. Pressure applied to motor inlet 212 enables rotation of air motor 200 to rotate inner cannula 162 when air motor 200 is advancing. The rotation of inner cannula 162 while the biopsy cutting operation is taking place assists in providing a clean cut. When air motor 200 is activated for rotation, air pressure flows from motor inlet 212, through air motor 200, and is vented to the atmosphere at motor exhaust 214. Pressure applied to motor inlet 212 is via motor line 154 and is controlled by a foot switch (not shown) or directly from a console (not shown). When air motor 200 is driven distally, spring 462 compressed to a compressed state 538. The biopsy cycles between aperture open (FIG. 14) and aperture closed (FIG. 15).

Figure 16:
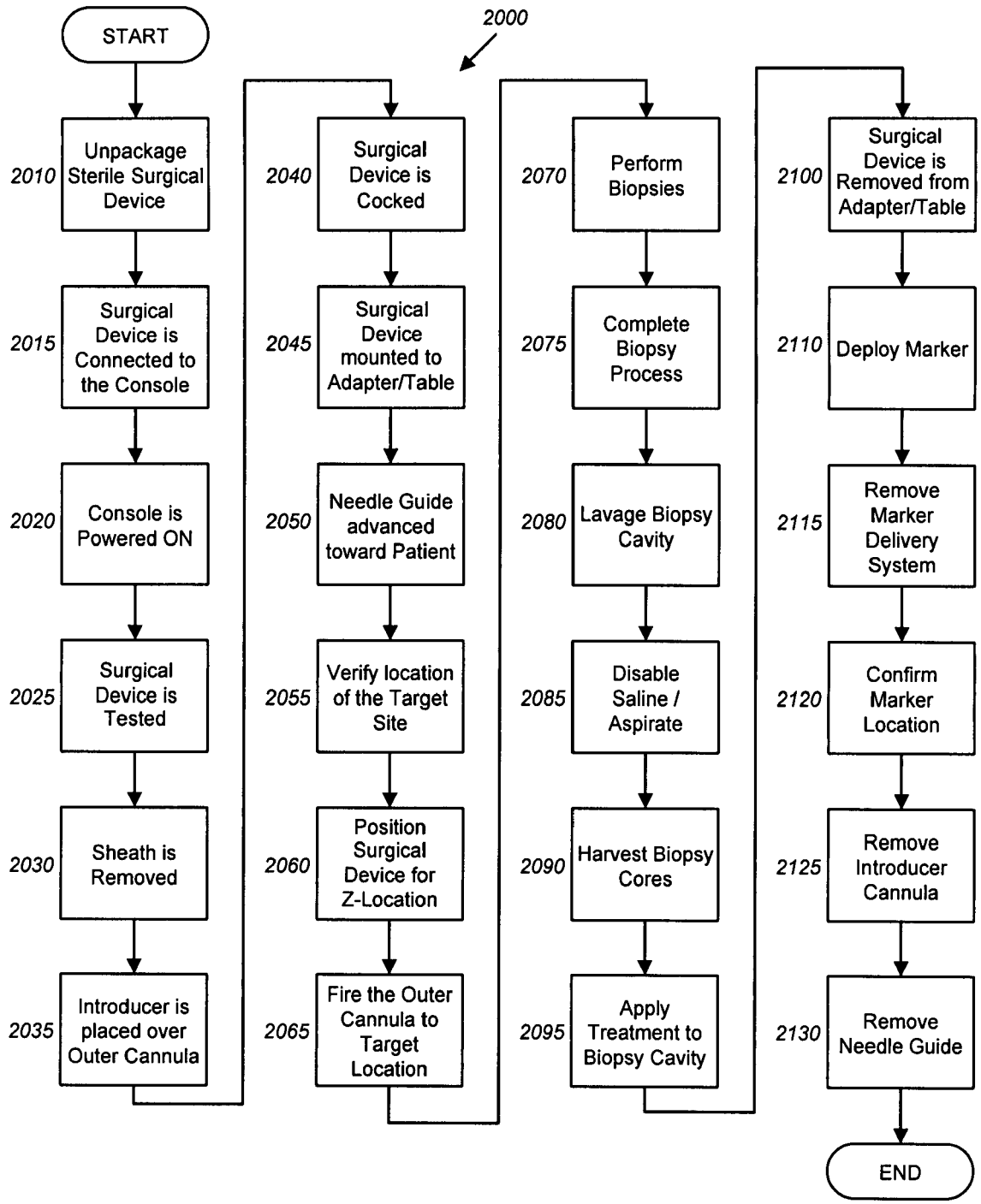
FIG. 16 illustrates a general process flow for using the surgical device of FIG. 1.
Figure 17:
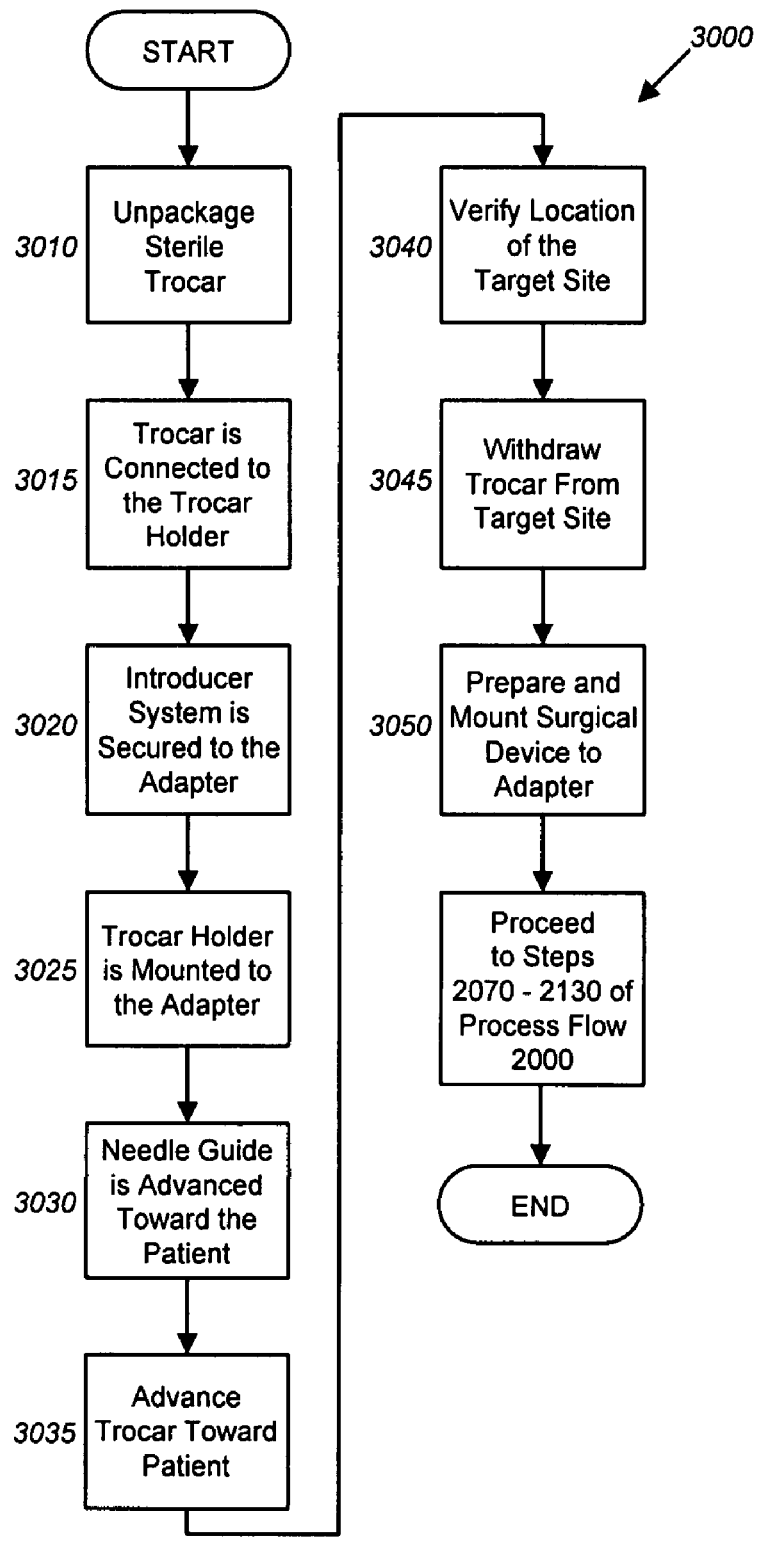
FIG. 17 illustrates a general process flow for using a trocar holder of FIG. 9 and the surgical device of FIG. 1.

FIG. 16 illustrates a general process flow 2000 for using an embodiment of surgical device 100. The process flow is an example of how surgical device 100 may be used in a hospital and/or doctor's office. Each of the steps, and their order, is merely exemplary of a typical usage of surgical device 100 and it is understood that deviations from general process flow 2000 in the addition of steps, omission of steps, reordering of steps, and repetition of steps may be performed based on clinical needs or other criteria. A general process flow 3000 for using a separate trocar 575 to create a pathway for cutting element 132 is shown in FIG. 17.

Referring now to FIG. 16, at step 2010, the sterile surgical device 100 is unpackaged from sealed sterile shipping/storage packaging. The package is removed from a storage area and placed into a console tray designed to hold surgical device 100 and the associated tubing and connectors prior to use. The console tray is typically designed to have a footprint that matches the packaging. The process then continues with step 2015.

At step 2015, surgical device 100 is connected to console 194 (see FIG. 1A). In general, console 194 provides air pressure and vacuum, as well as control logic, for surgical device 100. A user connects saline line 150, firing line 152, motor line 154, and biopsy line 156 to console 194. Saline line 150 may also be connected externally from console 194 to a saline bag. The process then continues with step 2020.

At step 2020, console 194 is powered on. Console 194 performs a self-test of it's internal systems in preparation for use with surgical device 100. For example, inputs, outputs, vacuum and pressure systems are tested for proper functionality. The process then continues with step 2025.

At step 2025, surgical device 100 is tested using console 194. A protective sheath (not shown) is typically a plastic tube and is placed over outer cannula 160 (see FIG. 4) without introducer cannula 104 in place. The protective sheath allows surgical device 100 to prime and test the saline delivery and aspiration systems. In general, the protective sheath allows a vacuum to be achieved within the system. The protective sheath is typically already placed over outer cannula 160 when shipped. Thus, the user typically confirms that the protective sheath is in place rather than placing it on separately. A "setup" mode button is pressed on console 194 to begin the testing process. The entire system is then primed with saline, including surgical device 100. Saline is pulled through outer cannula 160 and sucked into inner cannula 162 using aspiration vacuum. The saline is then pulled through the removable filter/collection canister 922 (see FIG. 11B). The user may then view collection canister 922 filling with saline to show that the system and surgical device 100 are working properly. The process then continues with step 2030

At step 2030, the sheath covering the outer cannula is removed upon completion of testing surgical device 100, console 194, and the saline system. The process then continues with step 2035.

At step 2035, the introducer system, including introducer cannula 104 and introducer hub 126 (see FIG. 1), is placed over outer cannula 160. An example of an introducer cannula 104 is described in co-pending U.S. patent application Ser. No. 10/649,068, entitled "INTRODUCTION SYSTEM FOR MINIMALLY INVASIVE SURGICAL INSTRUMENTS," filed Aug. 27, 2003 by Joseph L. Mark et al., the contents of which are included in their entirety herein. Alternatively, the introducer system may be locked into vertical portion 408 of adapter 112 (see FIGS. 7A and 17). The process then continues with step 2040.

At step 2040, surgical device 100 is cocked. Remote valve 800 is set to the cocked position (shown in FIG. 12A). The process then continues with step 2045. This step may also be performed after surgical device 100 is mounted in step 2045.

At step 2045, surgical device 100 is mounted to adapter 112 which in turn is mounted on a movable portion of a stereotactic table, Surgical device 100 is secured onto adapter 112 and latch 180 is engaged with adapter 112 for positive attachment (see FIG. 3). The mounting is performed by sliding surgical device 100 onto the rail portion 476 of adapter 112 (see FIG. 17). The process then continues with step 2050.

At step 2050, a needle guide (used to stabilize introducer cannula 104) is advanced toward the patient. For example, in the case of a breast biopsy the needle guide is advanced toward the patient's breast. This can be accomplished manually or by using the stereotactic table positioning controls. For example, using table controls to advance the needle guide includes enabling the table's motor and then inputting the appropriate X/Y location. The process then continues with step 2055.

At step 2055, the location of the target site is verified. Typically, stereotactic location pairs (e.g., two or more images taken from different angles) are used to confirm the location of introducer cannula 104 relative to the target site. Once the target location is confirmed, the process then continues with step 2060.

At step 2060, surgical device 100 is positioned given the Z-location of the target site. Typically, the Z location is a manual adjustment made by the user. Z positioning is stopped short by the exact distance of the firing stroke of surgical device 100. That is to say, the position of introducer cannula 104 is advanced to a position where, when outer cannula 160 is fired; the center of aperture 250 (see FIG. 4) is precisely located at the target site. The process then continues with step 2065.

At step 2065, outer cannula 160 is fired to the target site. Surgical device 100 is fired using remote valve 800. Outer cannula 160 is fired and trocar tip 134 rapidly pierces the patient's tissue to leave cutting element 132 at the target site (described in detail above with respect to FIGS. 1 and 4). The process then continues with step 2070.

At step 2070, the biopsy process is performed. Biopsy cores are severed and pulled through the system to collection canister 922 by the aspiration vacuum. Users typically rotate aperture 250 in a predetermined pattern to sample at a predetermined number of angles around the target site. For example, a user may rotate aperture 250 from positions at 10:00 to 12:00 to 2:00, taking a biopsy sample at each location. Moreover, the user may sample continuously around the target location. In a typical sampling, the user takes biopsy samples at 2:00, 4:00, 6:00, 8:00, 10:00, and 12:00 positions. In doing so, the user rotates aperture 250 using rotator 106 (see FIG. 1) when indicated by an alerting mechanism, such as an audible alarm or blinking light or a combination thereof. In an embodiment having an audible alarm, once the user hears the alarm, the user then has a predetermined time (which is adjustable) to turn rotator 106 and aperture 250, before the next biopsy sample is taken. For example, console 194 may be placed into biopsy mode which triggers an automatic sampling every five seconds. When console 194 beeps, the doctor may turn aperture 250 to the appropriate location at each and every beep. The process then continues with step 2075.

At step 2075, the biopsy process is completed and the user may verify that tissue has been resected from the patient and is trapped in collection canister 922. The process then continues with step 2080

At step 2080, biopsy cavity may be ravaged. The lavage function allows for the placement of markers in a clean cavity. It also allows for the clearing out of bodily fluids from collection canister 922 before removal and harvesting of the cores taken. To lavage the biopsy cavity, console 194 is set into lavage mode where aperture 250 is open, and saline flushes the system and the target site for about 30 seconds. The user may selectively shorten or lengthen the lavage time until clean fluid is seen passing through the collection canister 922. The process then continues with step 2085.

At step 2085, the saline supply is disabled and the target site/biopsy cavity is aspirated. Surgical device 100 is also aspirated which removes fluids, e.g. saline and bodily fluids, from the system. To aspirate the system, stopcock 890 (see FIG. 11B) or a selectively operable luer lock, is moved to close the saline supply and opens saline line 150 to atmosphere. Thus, with console 194 in lavage mode, a vacuum is pulled through the system and without saline; the aspiration removes any fluids in the system. Once the collection canister 922 is clear of saline, it can be removed without undue leaking of saline or bodily fluids to provide for a cleaner working environment for the user through reduced spillage of fluids. Moreover, removal of remote collection canister 922 allows the specimen to be taken to a radiograph machine so that images may be taken in real-time or near realtime while the patient remains prone over the stereotactic table. The process then continues with step 2090.

At step 2090, the biopsy cores are harvested from collection canister 922 (see FIG. 11B). The process then continues with step 2095.

At step 2095, a treatment may be applied to the biopsy cavity. Treatments may include, for example, saline wash, haemostatic agents, drugs, or other therapies may be applied or introduced to the target site through saline line 150 and outer cannula 160. The process then continues with step 2100.

At step 2100, surgical device 100 is removed from adapter 112 and the stereotactic table. For removal, latch lever 108 is pushed up by the user to unlock surgical device 100 from adapter 112. The user then slides surgical device 100 off of rail 476 (see FIG. 9A). Leaving introducer locked into adapter 112. Introducer and needle guide remain. At step 2100, surgical device 100 is removed from adapter 112 and is appropriately packaged for disposal and console 194 (see FIG. 1A) is powered off. Introducer cannula 104 remains partially within the patient and is attached to vertical portion 408 by hub snap feature 412 (see FIGS. 7 and 7A). Thus, introducer cannula 104 provides access at distal end 130 of introducer cannula 104 (see FIG. 1) to the target site for insertion of treatments, substances, and/or markers. Seal 410 substantially prevents introducer cannula 104 from leaking (e.g., as blood, saline, adjuvant treatments, etc.) material from the target site. The process then continues with step 2110.

At step 2110, if desired, a surgical site marker is deployed through introducer cannula 104. A marker delivery system (not shown) may be used that is sized to introducer's internal diameter and length. Thus, when a marker is deployed, leakage is reduced from introducer cannula 104 and the marker will be placed precisely in the location where tissue was resected at the target site. Examples of a suitable marker delivery system are disclosed in co-pending U.S. patent application Ser. No. 11/305,141 by Terry D. Hardin et al., filed on Dec. 16, 2005, the contents of which are disclosed herein in its entirety. A deployment pushrod will snap into introducer hub 126 to exactly locate the end of the deployment pushrod and mark at the exact location of the aperture that was used to sample. The surgical site marker is typically pushed down the lumen of introducer cannula 104 to provide a locating mechanism to ascertain the position of the target site in the future. The process then continues with step 2115.

At step 2115, the marker delivery system is removed from introducer cannula 104. Alternatively, the marker system and introducer cannula 104 may be removed at the same time by unlatching introducer hub 126 from adapter 112. The process then continues with step 2020.

At step 2120, the marker location is confirmed using an imaging modality (such as, e.g., stereotactic x-ray photography or ultrasound). The process then continues with step 2025.

At step 2125, introducer cannula 104 is removed from adapter 112 and is discarded. However, step 2125 is skipped when the user chooses to remove the marker delivery system and introducer cannula 104 in the same step as described above in step 2115. The process then continues with step 2030.

At step 2130, the needle guide is removed and discarded. Adapter 112 remains attached to the stereotactic table and may be cleaned if necessary. The process then ends.

In some cases a user of surgical device 100 may desire to use a separate trocar to create a pathway for surgical device 100. For example, in those embodiments where surgical device 100 includes a blunt tip end rather than trocar tip 134, it is desirable to use trocar 575 to facilitate the creation of the pathway. A general process flow for utilizing trocar 575 is set forth in FIG. 17.

At step 3010 the sterile trocar 575 is unpackaged from a sealed sterile shipping/storage package. The process then continues with step 3015.

At step 3015, trocar 575 is connected to trocar holder 540. Trocar holder 540 is a permanent piece that does not come into contact with bodily fluids. As such, it is reusable for multiple procedures. A portion of trocar 575 is engaged with seats 550, 552. In one embodiment, trocar holder 540 is provided with a clip 570 that snaps into engagement with a groove 573 formed on a sidewall of trocar 575 to fixedly attach trocar 575 to trocar holder 540. Once trocar 575 is engaged with trocar holder 540, the process then continues with step 3020.

At step 3020, the introducer system, including introducer cannula 104 and introducer hub 126 is locked into vertical portion 408 of adapter 112 (see FIGS. 7A and 17). The process then continues with step 3025.

Next, at step 3025, trocar holder 540 with trocar 575 secured thereto, is mounted to adapter 112, which in turn is mounted on a movable portion of a stereotactic table. More specifically, receiving grooves 542, 544 are engaged with edges 746 of adapter 112 and slid along adapter 112 until a bottom portion of trocar holder 540 reaches slot 488. At slot 488, trocar holder snaps into place to fixedly secure trocar holder 540 to adapter 112. Further, a tip of trocar 575, which is secured to trocar holder 540, enters into and extends through introducer cannula 104 as trocar holder 540 is slid along adapter 112. Once trocar holder 540 is secured to adapter 112, the process proceeds to step 3030.

Like the process flow described in connection with FIG. 16, at step 3030, a needle guide is advanced toward the patient. The process then continues with step 3035.

At step 3035, the trocar 575, with the introducer cannula 104 positioned therearound, is advanced toward the patient, through the needle guide, to create a pathway. This may be accomplished by using the stereotactic table positioning controls. The process then continues with step 3040.

At step 3040, the positioning of trocar 575 and/or introducer cannula 104 is verified to insure that the pathway created by trocar 575 leads to the desired target site. In one embodiment, stereotactic location pairs (e.g., two or more images taken from different angles) are used to confirm the location of trocar 575 and/or introducer cannula 104. Once the target is confirmed, the process then continues with step 3045.

At step 3045, trocar 575 is withdrawn from introducer cannula 104. In one embodiment, trocar holder 540 is released from slot 488 and slid backward along edges 746 of adapter 112, until trocar holder 540 (still carrying trocar 575) is disengaged with adapter 112. Once disengaged, clip 570 of trocar holder 540 is activated to release trocar 575.

In another embodiment, trocar 575 is released from trocar holder 540 (by activation of clip 570) and withdrawn from introducer cannula 104. Then, trocar holder 540 is released from slot 488 and slid backward along edges 746 of adapter 112 until holder is disengaged with adapter 112. In both embodiments, introducer cannula 104 remains in registration with the target site. Blood and other bodily fluids are prevented from flowing through intruder hub 126 by a normally closed seal therein. The process then proceeds to step 3050.

After trocar 575 is removed, at step 3050, surgical device 100 is then mounted to adapter 112 which is already secured to a movable portion of the stereotactic table. Prior to mounting surgical device 100 to adapter 112, steps 2010-2030, 2040 from the process flow described in connection with FIG. 16 are performed.

When mounting surgical device 100 to adapter 112, a cradle 114 of surgical device 100 is slid along edges 746 of adapter 112 until a front face surgical device 100 engages wall portion 408 and latch tongue 470 engages latch slot 472. Further, while surgical device 100 is slid along adapter 112, outer cannula 160 is inserted into introducer cannula 104 and is moved therethrough. When surgical device 100 is moved and locked into position on adapter 112, trocar tip 134 of outer cannula 160 extends outwardly from a distal end of introducer cannula 104 (see FIG. 4). Once surgical device 100 is mounted to adapter 112, the process follows steps 2070-2130 described in connection with FIG. 16.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

With regard to the processes, methods, heuristics, etc. described herein, it should be understood that although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes described herein are provided for illustrating certain embodiments and should in no way be construed to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary is made herein. In particular, use of the singular articles such as "a," "the," "said," etc, should be read to recite one or more of the indicated elements unless a claim recites an explicit limitation to the contrary.

What is claimed is:

1. A surgical device having a proximal end and a distal end, said surgical device comprising:
   an outer sleeve adapted to mount to a cradle top;
   an inner body housed within the outer sleeve, the inner body rotatable relative to the outer sleeve;
   a rotatable cutting element, a portion of which is housed within the inner body, said cutting element comprising an inner cannula and an outer cannula, the outer cannula defining a tissue receiving aperture, wherein both the outer and inner cannulae are configured for rotation relative to the outer sleeve;
   a spool engaged with said outer cannula;
   a motor engaged with said inner cannula; and
   a spring positioned between said spool and said motor, wherein said spring is configured for translating said spool
   distally, thereby translating said outer cannula towards the distal end of the surgical device, and
   wherein said motor is configured so that translation of the motor relative to the outer sleeve causes corresponding translation of said inner cannula.

2. The device of claim 1, wherein said motor is a rotary motor for rotating said inner cannula.

3. The device of claim 2, wherein said rotary motor is a pneumatic motor.

4. The device of claim 1, wherein said spool is pneumatically operated, and further comprising a remote valve for controlling the translation of said spool, said remote valve selectively operable in a first position to provide fluid pressure to move said pneumatic spool a cocked position, and said remote valve selectively operable in a second position to vent the fluid pressure, allowing said spring to move said spool and said outer cannula to a fired position.

5. The device of claim 1, further including an indicator for verifying the radial position of the tissue receiving aperture, wherein the indicator is one of coupled to and integral with a rotator.

6. The device of claim 5, wherein the indicator is configured as one of visual and tactile feedback.

7. The device of claim 1, wherein the cradle top that supports the outer sleeve is configured to releasably engage an adapter.

8. The device of claim 1, wherein a rotator is operably connected to the cutting element and to a suction line, wherein the rotator is free to rotate to at least limit twisting of the suction line, and wherein the rotator extends at least partially outside the inner body and the suction line extends through at least a portion of the rotator.

9. The device of claim 1, further comprising a collection port operably connected with said inner cannula, wherein said collection port receives tissue resected by said cutting element.

10. A medical device, comprising:
    a cutting element comprising an inner cannula and an outer cannula, the outer cannula defining a tissue receiving aperture and an inner cannula;
    a pneumatic spool for moving said outer cannula;
    a pneumatic motor for moving said inner cannula, wherein said inner cannula and said outer cannula cooperate to resect tissue; and
    a spring positioned between and operatively connected to said motor and said spool, said spring configured for translating said spool in a distal direction for placing the outer cannula in a fired position and wherein said spring is configured for translating said motor in a proximal direction that places the tissue receiving aperture in an open state.

11. The device of claim 10, wherein said pneumatic motor is also configured for selectively rotating said inner cannula.

12. The device of claim 10, further comprising:
    an outer sleeve adapted to mount to a cradle top; and
    an inner body disposed within the outer sleeve, the inner body rotatable relative to the outer sleeve;
    wherein a portion of the rotatable cutting element is housed within the inner body and both the outer and inner cannulae are configured for rotation relative to the outer sleeve.

13. The device of claim 1, wherein said spring translates said piston to a retracted position that places the tissue receiving aperture in an open state.

14. A surgical device having a proximal end and a distal end, said surgical device comprising:
    a sleeve adapted to mount to a cradle;
    an inner body disposed within the sleeve, the inner body rotatable relative to the sleeve;
    a rotatable cutting element, a portion of which is housed within the inner body, said cutting element comprising an inner cannula and an outer cannula, the outer cannula defining a tissue receiving aperture and an inner cannula, wherein both the outer and inner cannulae are configured for rotation relative to the sleeve;
    a pneumatically operated spool engaged with said outer cannula;
    a pneumatically operated piston engaged with said inner cannula;
    a spring positioned between said spool and said piston; and
    a biopsy cavity positioned proximally of the spring and a spool cavity positioned distally of the spring, and
    a remote valve for controlling the translation of said pneumatically operated spool and piston, said remote valve selectively operable in a first position to provide pressure to said spool cavity to move said pneumatic spool in a cocked position and vents pressure from said biopsy cavity to move said piston in the cocked position, and said remote valve selectively operable in a second position to vent pressure from said spool cavity and move said pneumatic spool and said outer cannula to a fired position;
    wherein said spool is translated distally to translate said outer cannula towards a distal end of the surgical device, and said piston translates said inner cannula towards said distal end to sever tissue.

15. The device of claim 10, further comprising a biopsy cavity disposed in the medical device, wherein the motor is configured to move in a distal direction when the biopsy cavity receives pressurized fluid and the spring is configured to translate the motor in the proximal direction when pressured fluid of the biopsy cavity is vented.

16. The device of claim 10, further comprising a spool cavity disposed in the medical device, wherein the spring is configured to move the spool in the distal direction when the spool cavity is vented.

17. The device of claim 10, wherein the spool is configured to translate in the proximal direction in response to fluid pressure.

18. The device of claim 10, wherein the motor is configured to translate in the distal direction in response to fluid pressure.

* * * * *